US007709697B2

(12) United States Patent
Raab

(10) Patent No.: US 7,709,697 B2
(45) Date of Patent: May 4, 2010

(54) TRANSGENIC PLANTS EXPRESSING CIVPS OR INTEIN MODIFIED PROTEINS AND RELATED METHOD

(75) Inventor: R. Michael Raab, Cambridge, MA (US)

(73) Assignee: Agrivida, Inc., Medford, MA (US)

( * ) Notice: Subject to any disclaimer, the term of this patent is extended or adjusted under 35 U.S.C. 154(b) by 561 days.

(21) Appl. No.: 10/886,393

(22) Filed: Jul. 7, 2004

(65) Prior Publication Data

US 2005/0125860 A1 Jun. 9, 2005

Related U.S. Application Data

(63) Continuation of application No. PCT/US03/00432, filed on Jan. 7, 2003.

(60) Provisional application No. 60/346,541, filed on Jan. 8, 2002.

(51) Int. Cl.

| | |
|---|---|
| ***A01H 1/00*** | (2006.01) |
| ***C12N 15/82*** | (2006.01) |
| ***C12N 15/87*** | (2006.01) |
| ***C07H 21/04*** | (2006.01) |

(52) U.S. Cl. ...................... 800/278; 536/23.7; 536/23.2

(58) Field of Classification Search ....................... None
See application file for complete search history.

(56) References Cited

U.S. PATENT DOCUMENTS

| | | | | |
|---|---|---|---|---|
| 5,496,714 | A | 3/1996 | Comb et al. | |
| 5,654,184 | A | 8/1997 | Curtiss et al. | |
| 5,780,708 | A | 7/1998 | Lundquist et al. | |
| 5,834,247 | A | 11/1998 | Comb et al. | |
| 5,981,835 | A | 11/1999 | Austin-Phillips et al. | |
| 6,013,863 | A | 1/2000 | Lundquist et al. | |
| 6,022,846 | A | 2/2000 | Van Ooijen et al. | |
| 6,160,208 | A | 12/2000 | Lundquist et al. | |
| 6,395,966 | B1 | 5/2002 | Mumm et al. | |
| 6,531,316 | B1 * | 3/2003 | Lassner et al. | 435/455 |
| 6,800,792 | B1 | 10/2004 | Howard et al. | |
| 6,858,775 | B1 | 2/2005 | Xu et al. | |
| 7,102,057 | B2 * | 9/2006 | Lanahan et al. | 800/284 |
| 2003/0159182 | A1 | 8/2003 | Tackaberry et al. | |
| 2003/0167533 | A1 | 9/2003 | Yadav et al. | |
| 2008/0115243 | A1 | 5/2008 | Raab et al. | |

FOREIGN PATENT DOCUMENTS

| | | |
|---|---|---|
| EP | 0602899 | 6/1994 |
| WO | WO 97/01642 | 1/1997 |
| WO | WO9701642 | 1/1997 |
| WO | WO 98/21348 | 5/1998 |
| WO | 00/36093 | 6/2000 |
| WO | WO0036093 | 6/2000 |
| WO | 00/52155 | 9/2000 |
| WO | WO00/52155 | 9/2000 |
| WO | 00/71701 | 11/2000 |
| WO | WO 0071701 | * 11/2000 |
| WO | 01/59091 | 8/2001 |

OTHER PUBLICATIONS

Chong et al 1998, The Journal of Biological Chemistry 273:10567-10577.*

Shmuel Peitrokovski, "Conserved Sequence Features Of Inteins (Protein Introns) and Their Use in Identifying New Inteins and Related Proteins" Aug. 10, 1994, Protein Science, vol. 3, pp. 2340-2350.

Davis et al., "Protein Splicing: The Lengths Some Proteins Will Go To" 1995, Antonie van Leeuwenhoek, vol. 67, pp. 131-137.

Wang et al., "Identification of an Unusual Intein in Chloroplast ClpP Protease of Chlamydomonas Eugametos" May 2, 1997, Journal of Biological Chemistry, vol. 272, No. 18, pp. 11869-11873.

Chong et al., "Modulation of Protein Splicing of The Saccharomyces Cerevisiae Vacuolar Membrane ATPase Intein" Apr. 24, 1998, Journal of Biological Chemistry, vol. 273, No. 17, pp. 10567-10577.

Frederick S. Gimble, "Invasion of a Multitude of Genetic Niches By Mobile Endonuclease Genes" Feb. 8, 2000, FEMS Microbiology Letters, vol. 185, pp. 99-107.

Shingledecker et al., "Reactivity of the Cysteine Residues in the Protein Splicing Active Center of the Mycobacterium Tuberculosis RecA intein" Mar. 1, 2000, Archives of biochemistry and biophysics, vol. 375, No. 1, pp. 138-144.

Francine B. Perler, "InBase: the Intein Database" Aug. 31, 2001, Nucleic Acids Research, vol. 30, No. 1. pp. 383-384.

Sun et al., Protein *trans*-Splicing To Produce Herbicide-Resistant Acetolactate Synthase Applied And Environmental Microbiology, Mar. 2001, p. 1025-1029.

Sun et al., "Protein *trans*-Splicing To Produce Herbicide-Resistant Acetolactate Synthase," Applied And Environmental Microbiology, vol. 67, No. 3, pp. 1025-1029 (Mar. 2001).

Morassutti et al., "Production Of A Recombinant Antimicrobial Peptide In Transgenic Plants Using A Modified VMA Intein Expression System," FEBS Letters, vol. 519, Nos. 1-3, pp. 141-146 (Apr. 2002).

Lixin Chen, Sriharsa Pradhan and Thomas C. Evans, Jr., "Herbicide Resistance from a Divided EPSPS Protein: The Split *Synechocystis* DnaE Intein as an In Vivo Affinity Domain", *Gene: An International Journal of Genes and Genomes*, vol. 263, pp. 39-48 (2001).

Yang, et al., "Intein-mediated assembly of a functional β-glucuronidase in transgenic plants," PNAS, vol. 100, No. 6, pp. 3513-3518 (2003).

Chin et al., Protein trans-splicing in transgenic plant chloroplast: Reconstruction of herbicide resistance from split genes, PNAS, vol. 100, No. 8, pp. 4510-4515 (2003).

(Continued)

*Primary Examiner*—Ashwin Mehta
*Assistant Examiner*—Li Zheng
(74) *Attorney, Agent, or Firm*—Volpe and Koenig, P.C.

(57) ABSTRACT

Transgenic plants that express CIVPS or intein modified proteins, compositions of matter comprising them, products of diverse applications made from the transgenic plants, methods to construct the transgenic plants containing CIVPS or intein modified genes, methods to express CIVPS or intein modified proteins in plants, and methods of using the transgenic plants.

41 Claims, 2 Drawing Sheets

OTHER PUBLICATIONS

Figure 1:
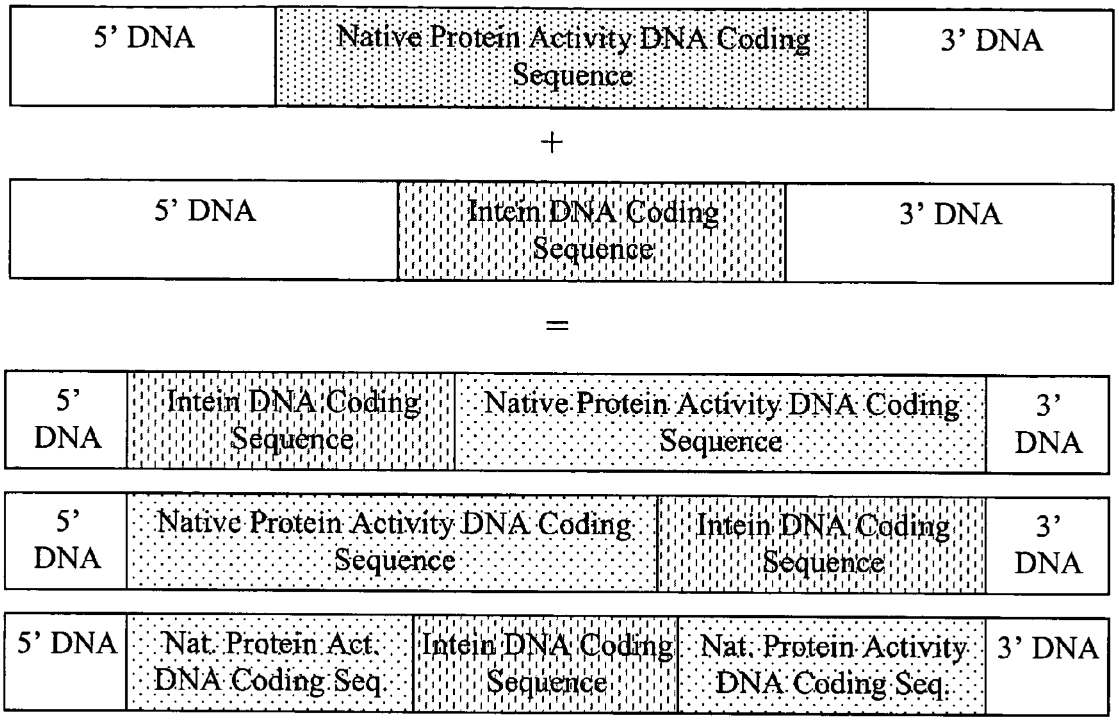

Chong, et al., "Single-column purification of free recombinant proteins using a self-cleavable affinity tag derived from a protein splicing element", Gene: An International Journal of Genes and Genomes, vol. 192, pp. 271-281 (1997).

Aspegren, K., et al., Secretion of Heat-Stable Fungal β-Glucanase from Transgenic, Suspension-Cultured Barley Cells, *Molecular Breeding*, 1995, pp. 91-99.

Birch, R.G., Plant Transformation: Problems and Strategies for Practical Application, *Annual Review of Plant Physiology and Plant Molecular Biology*, vol. 48, Jun. 1997, pp. 297-326.

Bird, C.R., et al., The Tomato Polygalacturonase Gene and Ripening-Specific Expressions in Transgenic Plants, *Plant Molecular Biology*, 1988, pp. 651-662.

Brederode, F.T., et al., Complete Nucleotide Sequence of Alfalfa Mosaic Virus RNA 4, *Nucleic Acids Research*, vol. 8, No. 10, 1980, pp. 2213-2223.

Broothaerts, W., et al., Gene Transfer to Plants by Diverse Species of Bacteria, *Nature*, vol. 433, Feb. 2005, pp. 629-633/.

Cameron, D.C., et al., Metabolic Engineering of Propanediol Pathways, *Biotechnology Progress*, 1998, pp. 116-125.

Chen, L., et al., "Herbicide Resistance from a Divided EPSPS Protein: The Split *Synechocystis* DnaE Intein as an In Vivo Affinity Domain", *Gene: An International Journal of Genese and Genomes*, vol. 263, pp. 39-48 (2001).

Cheon, B.Y., et al., Ovexpression of Human Erythropoietin (EPO) Affects Plant Morphologies: Retarded Vegetative Growth in Tobacco and Male Sterility in Tobacco and Arabidopsis, *Transgenic Research*, 2004, pp. 541-549.

Chih-Ching, C., et al., Establishment of an Efficient Medium for Anther Culture of Rice Through Comparative Experiments of the Nitrogen Sources, *Scientia Sinica*, vol. 18, No. 3, 1975, pp. 659-668.

Chin, H., et al., Protein trans-splicing in transgenic plant chloroplast: Reconstruction of herbicide resistance from split genes, *PNAS*, vol. 100, No. 8, pp. 41510-4515 (2003).

Chong, et al., "Modulation of Protein Splicing of the *Saccharomyces cerevisiae* Vacuolar MembraneATPase Intein", Apr. 24, 1998, *Journal of Biological Chemistry*, vol. 273, No. 17, pp. 10567-10577.

Chong, et al., "Single-column purification of free recombinant proteins using a self-cleavable affinity tag derived from a protein splicing element", *Gene: An International Journal of Genese and Genomes*, vol. 192, pp. 271-281 (1997).

Clarke, Neil D., "A Proposed Mechanism for the Self-Splicing of Proteins," Proceedings of the National Academy of Science, USA, vol. 91, pp. 11084-11088, Nov. 1994.

Coruzzi, G., et al., Tissue-Specific and Light-Regulated Expression of Pea Nuclear Gene Coding the Small Subunit of Ributose-1, 5-Bisphosphate Carboxylase, *The EMBO Journal*, 1984, 1671-1679.

Dai, Z., et al., Expression of Acidothermus Cellulolyticus Endoglucanase E1 in Transgenic Tobacco: Biochemical Characteristics and Physiological Effects, *Transgenic Research*, 2000, pp. 43-54.

Dai, Z., et al., Improved Plant-Based Production of E1 Endoglucanase Using Potato: Expression Optimization and Tissue Targeting, *Molecular Breeding*, 2000, pp. 277-285.

Dale, Bruce E., Biobased Industrial Products: Bioprocess Engineering When Costs Really Count, *Biotechnology Progress*, 1999, pp. 775-776.

Derbyshire, et al., "Lightning Strikes Twice: Intron-Intein Coincidence," Proceedings of the National Academy of Science, USA, vol. 95, pp. 1356-1357, Feb. 17, 1998.

Evans, et al., "Semisynthesis of Cytotoxic Proteins Using a Modified Protein Splicing Element," Protein Science, vol. 7: pp. 2256-2264 (1998).

Gimble, Frederick S., "Invasion of a Multitude of Genetic Niches by Mobile Endonuclease Genes", Feb. 8, 2000, *FEMS Microbiology Letters*, vol. 185, pp. 99-107.

Gordon-Kamm, et al., "Transformation of Maize Cells and Regeneration of Fertile Transgenic Plants," The Plant Cell, vol. 2, pp. 603-618, Jul. 1990.

Gupta, P.K., et al., Shoot Multiplication from Mature Trees of Douglas Fir and Sugar Pine, *Plant Cell Reports*, vol. 4, 1985, pp. 177-179.

Higgins, T.J.V., Synthesis and Regulation of Major Proteins in Seeds, *Annual Review of Plant Physiology*, 1984, pp. 191-221.

Hood, E.E., et al., Commercial Production of Avidin from Transgenic Maize: Characterization of Transformant, Production, Processing Extraction and Purification, *Molecular Breeding*, 1997, pp. 291-306.

Horsch, R.B., et al, A Simple and General Method for Transferring Genes into Plants, *Science*. Mar. 1985, pp. 1229-1231.

Ingram, L.O., et al., Enteric Bacterial Catalysts for Fuel Ethanol Production, *Biotechnology Progress*, 1999, pp. 856-866.

Klein, T.M., et al., High-Velocity Microprojectiles for Delivering Nucleic Acids Into Living Cells, *Nature*, vol. 327, May 1987, pp. 70-73.

Lai et al., "Structural Characterization of Human Erythropoietin." The Journal of Biological Chemistry, vol. 261, pp. 3116-3121, Mar. 5, 1986.

Matsumoto, S., et al., Characterization of Human Glycoprotein (Erythropoietin) Produced in Cultured Tobacco Cells, *Plant Molecular Biology*, 1995, pp. 1163-1172.

Morassutti, et al., "Production of a Recombinant Antimicrobial Peptide in Transgenic Plants Using a Modified VMA Intein Expressing System," *FEBS letters*, vol. 519, Nos. 1-3, pp. 141-146 (Apr. 2002).

Perler, Francine B., "InBase: The Intein Database," *Nucleic Acids Research*, 2002, vol. 30, No. 1, pp. 383, 384.

Parsons, T.J., et al., Transformation of Poplar by Agrobacterium Tumefaciens, *Biotechnology*, vol. 4, Jun. 1986, pp. 533-536.

Perler, Francine B., "InBase: The Intein Database," *Nucleic Acids Research*, 2002, vol. 30, No. 1, pp. 383, 384.

Pietrokovski, Samuel, "Conserved Sequence Features of Inteins (Protein Introns) and Their Use in Indentifying New Inteins and Related Proteins," Protein Science, vol. 3, pp. 2340-2350, Aug. 10, 1994.

Ryan, A.J., et al., Genomic Sequence of a 12S Seed Storage Protein from Oilseed Rape, *Nucleic Acids Research*, vol. 17, No. 9, 1989, p. 3584.

Shimamoto, K., et al., Fertile Transgenic Rice Plants Regenerated from Transformed Protoplasts, *Nature*, vol. 338, Mar. 1989, pp. 274-276.

Shingledecker, et al., "Reactivity of the Cysteine Residues in the Protein Splicing Active Center of the Mycobacterium Tuberculosis RecA Intein", Mar. 1, 2000, *Archives of Biochemistry and Biophysics*, vol. 375, No. 1, pp. 138-144.

Sijmons, P.C., et al., Production of Correctly Processed Human Serum Albumin in Transgenic Plants, *Biotechnology*, vol. 8, Mar. 1990, pp. 217-221.

Sun, et al., "Protein Trans-Splicing to Produce Herbicide-Resistant Acetolactate Synthase," Applied and Environmental Microbiology, Mar. 2001, pp. 1025-1029.

Van Den Broeck, G., et al., Targeting of a Foreign Protein to Chloroplasts by Fusions to the Transmit Peptide from the Small Subunit of Ribulose 1,5-Bisphosphate Carboxylase, *Nature*, vol. 313, Ksmistu 1985, pp. 358-363.

Wallace, Carmichael J.A., "The Curious Case of Protein Splicing: Mechanistic Insights Suggested by Protein Semisynthesis," Protein Science, vol. 2, pp. 697-705 (1993).

Wang, et al., "Identification of an Unusual Intein in Chloroplast CipP Protease of Chlamydomonas Eugametos", May 2, 1997, *Journal of Biological Chemistry*, vol. 272, No. 18, pp. 11869-11873.

Yang, J., et al., "Intein-mediated assembly of a functional β-glucuronidase in transgenic plants", *PNAS*, vol. 100, No. 6, pp. 3513-3518 (2003).

Altintas, M. M., et al, "Improvement of Ethanol Production from Starch by Recombinant Yeast Through Manipulation of Environmental Factors," *Enzyme and Microbial Technology*, vol. 31, No. 5, 2002, pp. 640-647.

Aspegren, K., et al., "Secretion of Heat-Stable Fungal β-Glucanase from Transgenic, Suspension-Cultured Barley Cells," *Molecular Breeding*, 1995, pp. 91-99.

Birch, R.G., "Plant Transformation: Problems and Strategies for Practical Application," *Annual Review of Plant Physiology and Plant Molecular Biology*, vol. 48, Jun. 1997, pp. 297-326.
Bird, C.R., et al., "The Tomato Polygalacturonase Gene and Ripening-Specific Expressions in Transgenic Plants," *Plant Molecular Biology*, 1988, pp. 651-662.
Brederode, Ft., et al., "Complete Nucleotide Sequence of Alfalfa Mosaic Virus RNA 4," *Nucleic Acids Research*, vol. 8, No. 10, pp. 2213-2223.
Broothaerts, W., et al., "Gene Transfer to Plants by Diverse Species of Bacteria," *Nature*, vol. 433, Feb. 2005, pp. 629-633/.
Cameron, D.C., et al., "Metabolic Engineering of Propanediol Pathways," *Biotechnology Progress*, 1998, pp. 116-125.
Chen, Lixin; Pradhan, Sriharsa and Evans, Jr., Thomas C., "Herbicide Resistance from a Divided EPSPS Protein: The Split *Synechocystis* DnaE Intein as an In Vivo Affinity Domain", *Gene: An International Journal of Genes and Genomes*, vol. 263, pp. 39-48 (2001).
Cheon, B.Y., et al., "Ovexpression of Human Erythropoietin (EPO) Affects Plant Morphologies: Retarded Vegetative Growth in Tobacco and Male Sterility in Tobacco and Arabidopsis," *Transgenic Research*, 2004, pp. 541-549.
Chih-Ching, C., et al., "Establishment of an Efficient Medium for Anther Culture of Rice Through Comparative Experiments on the Nitrogen Sources," *Scientia Sinica*, vol. 18, No. 3, 1975, pp. 659-668.
Chin, Hang Gyeong, et al., Protein trans-spliciFlan transgenic plant chloroplast: Reconstruction of herbicide resistance from split genes, *PNAS*, vol. 100, No. 8, pp. 4510-4515 (2003).
Chong, et al. ., "Single-column purification of free recombinant proteins using a self-cleavable affinity tag derived from a protein splicing element", *Gene: An International Journal of Genes Genomes*, vol. 192, pp. 271-281 (1997).
Coruzzi, G., et al., "Tissue-Specific and Light-Regulated Expression of Pea Nuclear Gene Coding the Small Subunit of Ribulose-1, 5-Bisphosphate Carboxylase," *The EMBO Journal*, 1984, 1671-1679.
Dai, Z., et al., "Expression of Acidothermus Cellulolyticus Endoglucanase E1 in Transgenic Tobacco: Biochemical Characteristics and Physiological Effects," *Transgenic Research*, 2000, pp. 43-54.
Dai, Z., et al., "Improved Plant-Based Production of E1 Endoglucanase Using Potato: Expression Optimization and Tissue Targeting," *Molecular Breeding*, 2000, pp. 277-285.
Dale, Bruce E., "Biobased Industrial Products: Bioprocess Engineering When Costs Really Count," *Biotechnology Progress*, 1999, pp. 775-776.
Davis, E., et al., "Novel Structure of the recA Locus of Mycobacterium Tuberculosis Implies Processing of the Gene Product," *Journal of Bacteriology*, vol. 173, No. 18, Sep. 1991, pp. 5653-5662.
Davis, E., et al., "Protein Splicing in the Maturation of M. Tuberculosis RecA Protein: A Mechanism for Tolerating a Novel Class of Intervening Sequence," Cell Press, vol. 71, Oct. 16, 1992, pp. 201-210.
Evans, et al., "Semisynthesis of Cytotoxic Proteins Using a Modified Protein Splicing Element," *Protein Science*, vol. 7: (1998), pp. 2256-2264.
Gangopadhyay, J.P., et. al., "In Vitro Splicing of Erythropoietin by the Mycobacterium Tuberculosis RecA Intein Without Substituting Amino Acids at the Splice Junctions," *Biochimica et Biophysica Acta*, vol. 1619, (2003), pp. 193-200.
Guilley, H., et al., "Transcription of Cauliflower Mosaic Virus DNA: Detection of Promoter Sequences, and Characterization of Transcripts," *Cell*, vol. 30, Oct. 1982, pp. 763-773.
Gupta, P.K., et al., "Shoot Multiplication from Mature Trees of Douglas Fir and Sugar Pine," *Plant Cell Reports*, vol. 4, 1985, pp. 177-179.
Higgins, T.J.V., "Synthesis and Regulation of Major Proteins in Seeds," *Annual Review of Plant Physiology*, 1984, pp. 191-221.
Hirata, R., et al., "Molecular Structure of a Gene, VMA1, Encoding the Catalytic Subunit of $H^+$-Translocating Adenosine Triphosphatase fro Vacuolar Membranes of *Saccharomyces cerevisiae," The Journal of Biological Chemistry*, vol. 265, No. 12, Apr. 25, 1990, pp. 6826-6733.
Hood, E.E., et al., "Commercial Production of Avidin from Transgenic Maize: Characterization of Transformant, Production, Processing, Extraction and Purification," *Molecular Breeding*, 1997, pp. 291-306.
Horsch, R.B., et al, "A Simple and General Method for Transferring Genes into Plants," *Science*, Mar. 1985, pp. 1229-1231.
Ingram, L.O., et al., "Enteric Bacterial Catalysts for Fuel Ethanol Production," *Biotechnology Progress*, 1999, pp. 856-866.
Kane, P.M., et. al., "Protein Splicing Converts the Yeast TFP1 Gene Product to the 69-kD Subunit of the Vacuolar H+-Adenosine Triphosphatase," *Science*, New Series, vol. 250, No. 4981, Nov. 2, 1990, pp. 651-657.
Klein, T.M., et al., "High-Velocity Microprojectiles for Delivering Nucleic Acids Into Living Cells," *Nature*, vol. 327, May 1987, pp. 70-73.
Lai et al., "Structural Characterization of Human Erythropoietin." *The Journal of Biological Chemistry*, vol. 261, pp. 3116-3121, Mar. 5, 1986.
Latif, F., et al., "Production of Ethanol and Xylitol from Corn Cobs by Yeasts," *Bioresource Technology*, vol. 77, 2001, pp. 57-63.
Lynd, L.R., et al., "Biocommodity Engineering," *Biotechnology Progress*, vol. 15, 1999, pp. 777-793.
Mansfield, S.D., et al., "Substrate and Enzyme Characteristics that Limit Cellulose Hydrolysis," *Biotechnology Progress*, vol. 15, 1999, pp. 804-816.
Montvalvo-Rodriguez, R., et al., "Autohydrolysis of Plant Polysaccharides Using Transgenic Hyperthermophilic Enzymes," *Biotechnology and Bioengineering*, vol. 2, 2000, pp. 151-159.
Matsumoto, S., et al., "Characterization of Human Glycoprotein (Erythropoietin) Produced in Cultured Tobacco Cells," *Plant Molecular Biology*, 1995, pp. 1163-1172.
Olsson, L., et al., "Fermentation of lignocellulosic Hydrolysates for Ethanol Production," *Enzyme and Microbial Technology*, vol. 18, 1996, pp. 312-331.
Parsons, T.J., et al., "Transformation of Poplar by Agrobacterium Tumefaciens," *Biotechnology*, vol. 4, Jun. 1986, pp. 533-536.
Perler, Francine B., "InBase: The Intein Database," *Nucleic Acids Research*, 2002, vol. 30, No. 1, pp. 383, 384.
Perler, F.B., et al., "Protein Splicing Elements; Inteins and Exteins—A Definition of Terms and Recommended Nomenclature", *Nucleic Acids Research*, vol. 22, No. 7, Feb. 24, 1993, pp. 1125-1127.
Pietrokovski, Samuel, "Conserved Sequence Features of Inteins (Protein Introns) and Their Use in Identifying New Iteins and Related Proteins," *Protein Science*, vol. 3, pp. 2340-2350, Aug. 10, 1994.
Poirier, Yves, "Green Chemistry Yields a Better Plastic," *Nature Biotechnology*, vol. 17, Oct. 1999, pp. 960-961.
Rocha-Sosa, M., et al., "Both Developmental and Metabolic Signals Activate the Promoter of a Class I Patatin Gene," The EMBO Journal, vol. 8, No. 1, 1989, pp. 23-29.
Schreier, P.H., et al., ,,The Use of Nuclear-Encoded Sequences to Direct the Light-Regulated Synthesis and Transport of a Foreign Protein into Plant Chloroplasts, *The EMBO Journal*, vol. 4, No. 1, 1985, pp. 25-32.
Smeekens, et al., "Protein Transport into and Within Chloroplasts," *Trends in Biochemical Sciences*, vol. 15, Feb. 1990, pp. 73-76.
Sreenath, H.K., et al., "Production of Ethanol from Wood Hydrolyzate by Yeasts," *Bioresource Technology*, vol. 72, No. 3, 2000, pp. 253-260.
Staub, J.M., et al., "High-Yield Production of a Human Therapeutic Protein in Tobacco Chloroplasts," *Nature Biotechnology*, vol. 18, Mar. 2000, pp. 333-338.
Sun, et al., "Protein Trans-Splicing to Produce Herbicide-Resistant Acetolactate Synthase," *Applied and Environmental Microbiology*, Mar. 2001, pp. 1025-1029.
Tague, B.W., et al., "A Short Domain of the Plant Vacuolar Protein Phytohemagglutinin Targets Invertase to the Yeast Vacuole," *The Plant Cell*, vol. 2, Jun. 1990, pp. 533-546.
Taylor, F., et al., "Dry-Grind Process for Fuel Ethanol by Continuous Fermentation and Stripping," *Biotechnology Progress*, vol. 16, 2000. pp. 541-547.
Tingey, S.V., et al., "Glutamine Synthetase Genes of Pea Encode Distinct Polypeptides Which are Differentially Expressed in Leaves, Roots and Nodules," *The EMBO Journal*, vol. 6, No. 1, 1987, pp. 1-9.

Ulgen, K.O., et. al., "Bioconversion of Starch Into Ethanol by a Recombinant *Saccharomyces cerevisiae* Strain YPG-AB," *Process Biochemistry*, vol. 37, 2002, pp. 1157-1168.

Von Heijne, G., "Towards a Comparative Anatomy of N-Terminal Topogenic Protein Sequences," *Journal of Molecular Biology*, vol. 189, 1986, pp. 239-242.

Wenzler, H.C., et al., "Analysis of a Chimeric Class-I Patatin-GUS Gene in Transgenic Potato Plants: High-Level Expression in Tubers and Sucrose-Inducible Expressions in Cultured Leaf and Stem Explants," *Plant Molecular Biology*, vol. 12, 1989, pp. 41-50.

Wood, D.W., et al., "Optimized Single-Step Affinity Purification with a Self-Cleaving Intein Applied to Human Acidic Fibroblast Growth Factor," *Biotechnology Progress*, vol. 16, 2000, pp. 1055-1063.

Xu, M., et al., "In Vitro Protein Splicing of Purified Precursor and the Identification of Branched Intermediate," *Cell*, vol. 75, Dec. 31, 1993, pp. 1371-1377.

Xu, M., et al., "The Mechanism of Protein Splicing in its Modulation by Mutation," *The EMBO Journal*, vol. 15, No. 19, 1996, pp. 5146-5153.

Yang, Jianjun, et al., "Intein-mediated assembly of a functional β-glucuronidase in transgenic plants", *PNAS*, vol. 100, No. 6, pp. 3513-3518 (2003).

Ziegler, M.T., et al., "Accumulation of Thermostable Endo-1,4-β-D-Glucanase in the Apoplast of Arabidposis Thaliana Leaves," *Molecular Breeding*, vol. 6, 2000, pp. 37-46.

* cited by examiner

TRANSGENIC PLANTS EXPRESSING CIVPS OR INTEIN MODIFIED PROTEINS AND RELATED METHOD

REFERENCE TO RELATED APPLICATIONS

This application is a continuation of International Application No. PCT/US03/00432 filed Jan. 7, 2003 which in turn claims priority from U.S. provisional application No. 60/346,541 filed Jan. 8, 2002, which are both incorporated by reference as if fully set forth.

The sequence listing titled “Sequence Listing,” which was created on Mar. 13, 2009 and had a file size 26.3 kilo-bytes, is incorporated by reference herein as if fully set forth.

FIELD OF THE INVENTION

The present invention relates to transgenic plants expressing CIVPS or intein modified proteins, methods for the production of the transgenic plants, methods for the expression of CIVPS or intein modified proteins in plants, and various uses of and products containing the transgenic plants expressing CIVPS or intein modified proteins.

BACKGROUND

Since fossil fuels are non-renewable resources, adequate supplies of energy and organic feedstocks need to be secured for the future. A transition to sustainable resources requires new technologies for the construction of improved feedstocks, the design of efficient processes to convert the feedstocks into valuable products, and/or the design of products that efficiently utilize an altered substrate spectrum. This transformation will create benefits such as decreased pollution from energy production and use, decreased pollution from chemical manufacturing processes, increased sustainability through the utilization of renewable natural resources and organic waste products as substrates, decreased dependence on foreign country’s raw materials, and an increase in local economies and markets involved in the production of new substrates.

Plant biomass is one sustainable resource that can help meet future feedstock requirements. The use of plants as substrates for energy, chemical, pharmaceutical, and organic feedstock takes advantage of existing large-scale agricultural production, uses energy from the sun to incorporate carbon dioxide into plants via photosynthesis, and has fewer environmentally hazardous by-products. By using photosynthesis, plants make the carbon dioxide removed from the air available for the production of energy, chemicals, and agricultural products. Finding ways to effectively redistribute this carbon in forms that are readily and economically employable remains a challenge.

The production of chemical feedstocks and fuels from plant biomass is still in its infancy. Starch-based raw materials, for example, may be applied to the production of commodity or specialty chemical products. Poor substrate and strain availability hampering bioconversion, along with real or perceived safety issues related to containment, and a lack of economic viability, have made progress in this area particularly slow. Non-cellulosic biomass, such as corn starch, compares favorably with fossil resources on a mass basis, but is too costly. Cellulosic biomass, such as short-rotation poplar, pine, switchgrass, corn stover, sugar cane bagasse, waste paper sludge, and municipal solid waste, in contrast, is cost competitive in terms of both mass and energy. Cellulosic biomass, because of its complex structure, is nevertheless difficult to process. Currently, cellulosic biomass requires pretreatment with strong acids, bases, and/or other chemicals for use as a substrate for fuel, e.g. ethanol, or for chemical production, e.g. paper products. This pretreatment efficiently exposes polymeric subunits, primarily hexoses, pentoses, and phenolic compounds, which are then cleaved and used as substrates, but is expensive. One alternative to the use of more hazardous chemicals is the use of enzymes, although it is less cost effective.

Recombinant DNA technology has been applied to alter microorganisms to perform substrate bioconversion at reduced costs, thus expanding the use of microorganisms, and increasing the number of products that are produced. For example, plant cells that express lignocellulosic degrading enzymes have been constructed, although they rarely differentiate and regenerate into complete plants due to decomposition of structural components. In cases where they differentiate into complete plants, e.g. with lignin and cellulose substrates, the enzyme activities are low and the plants require further processing. Attempts to combine pretreatment of substrate biomass with fermentation have encountered difficulties as well, in part because of mass transfer limitations and interference with the fermenting organism.

CIVPS or inteins are in-frame, self-cleaving peptides that generally occur as part of a larger precursor protein molecule. CIVPS or inteins differ from other proteases or zymogens in several fundamental ways. Unlike proteases that cleave themselves or other proteins into multiple, unligated polypeptides, CIVPS or inteins have the ability to both cleave and ligate in either cis or trans conformations. Thus as opposed to terminal cleavage that would result from the reaction of a protease on a protein, CIVPS or inteins have the ability to cleave at multiple sites, and ligate the resulting protein fragments. This cleavage is induced under specific conditions and can be engineered using molecular biology techniques. CIVPS or inteins have been described in the literature in *Sacchromyces cerevisiae* (Kane et. al., Science 250:651; Hirata et al., J. Bio. Chem. 265:6726 (1990)), *Mycobacterium tuberculosis* (Davis et al., J. Bact. 173:5653 (1991), Davis et al., Cell 71:1 (1992)), *Thermococcus litoralis* (Perler, et al., PNAS 89:5577 (1992)), and in other organisms, but do not occur naturally in plants.

Accordingly, there is a need for providing novel methods for producing energy and other pharmaceutical or industrial products from more easily renewable sources, such as by modifying plants in a manner such that they may be used as energy and chemical feedstocks.

SUMMARY

The present invention provides for genetically recombinant plants, their parts, plantlets, seeds, seedlings, and their progeny (collectively referred to as “plants”), which may contain single or multiple exogenous gene sequences, each being interrupted by, or fused to single or multiple Controllable InterVening Protein Sequence (CIVPS) or intein sequences, or a combination of a CIVPS or intein sequence, and optionally regulatory sequences suitable for gene expression and transformation of a plant. The modified gene sequences may be expressed constitutively or transiently, throughout the entire plant or in specific tissues, or any combination thereof encompassing both single and multiple CIVPS or intein modified gene sequences. In different embodiments of the invention, any modified gene sequence, or set of modified gene sequences, may be expressed in any or all tissues constitutively or at specific times.

The invention also relates to methods of producing transgenic plants comprising CIVPS or intein modified genes, e. g. by first constructing a piece of DNA comprising the parent CIVPS or intein modified gene, and transforming the plant with the construct.

The invention also relates to methods of producing an CIVPS or intein modified protein(s) in transgenic plants, e. g. by transforming the plant, or plant cells, with a single or multiple modified gene sequence(s), and expressing the CIVPS or intein modified protein(s). In one preferred embodiment the gene sequences may be expressed at any time. In another embodiment, prior to the protein(s) being spliced it preferably is(are) provided with a substantially different activity(ies) and/or structural property(ies). The spliced protein product(s) has(have) its(their) activity(ies) unveiled, unless inhibited by an exogeneously added or endogeneously produced molecule(s) analogous to the non-CIVPS or intein modified protein parent sequence. The CIVPS or intein modified gene products may be expressed in large quantities and recovered from the plant material. Alternatively, the plant or plant material may itself be used as a source of CIVPS or intein modified gene products.

The invention also provides for the use of CIVPS or intein modified gene products expressed in plants, the use of transgenic plants expressing CIVPS or intein modified genes in animal feed, or the use of transgenic plants expressing CIVPS or intein modified genes in batch, semi-batch, and continuous industrial processes for the production of fuels, chemical products, animal food or food additives, pharmaceuticals, paper, paper products, and for vaccine delivery and the remediation of waste materials.

Other objects, advantages and features of the present invention will become apparent to those skilled in the art from the following brief description of the drawings and discussion.

BRIEF DESCRIPTION OF THE DRAWING(S)

FIG. 1 illustrates the construction of an CIVPS or intein modified protein coding DNA sequence by constructing an CIVPS or intein modified protein DNA coding sequence constructed by fusion of an CIVPS or intein coding sequence to the coding sequence of a protein of a purported activity, at either the 3' end of the gene, the 5' end of the gene, or internally, within the protein gene. Other variants are possible by combining any of the three resulting CIVPS or intein modified protein coding sequences shown in FIG. 1.

Figure 2:
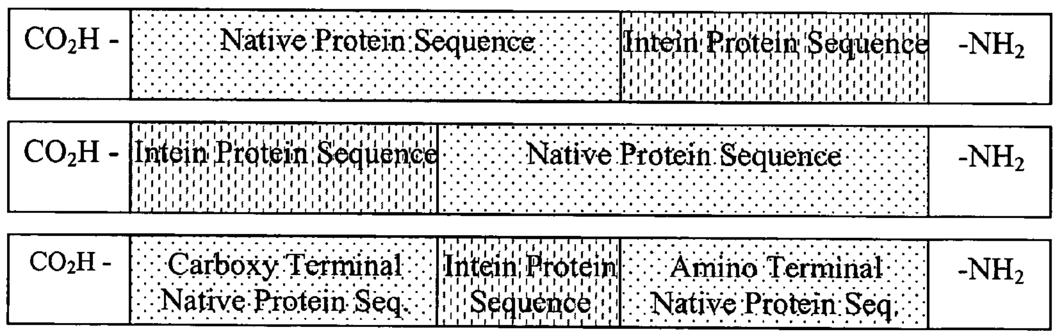

FIG. 2 illustrates one configuration of the resulting CIVPS or intein modified proteins, or components thereof. This figure demonstrates the case of a single CIVPS or intein modified protein. Multiple native protein sequences, however, may be combined with single or multiple CIVPS or inteins as well.

Figure 3:
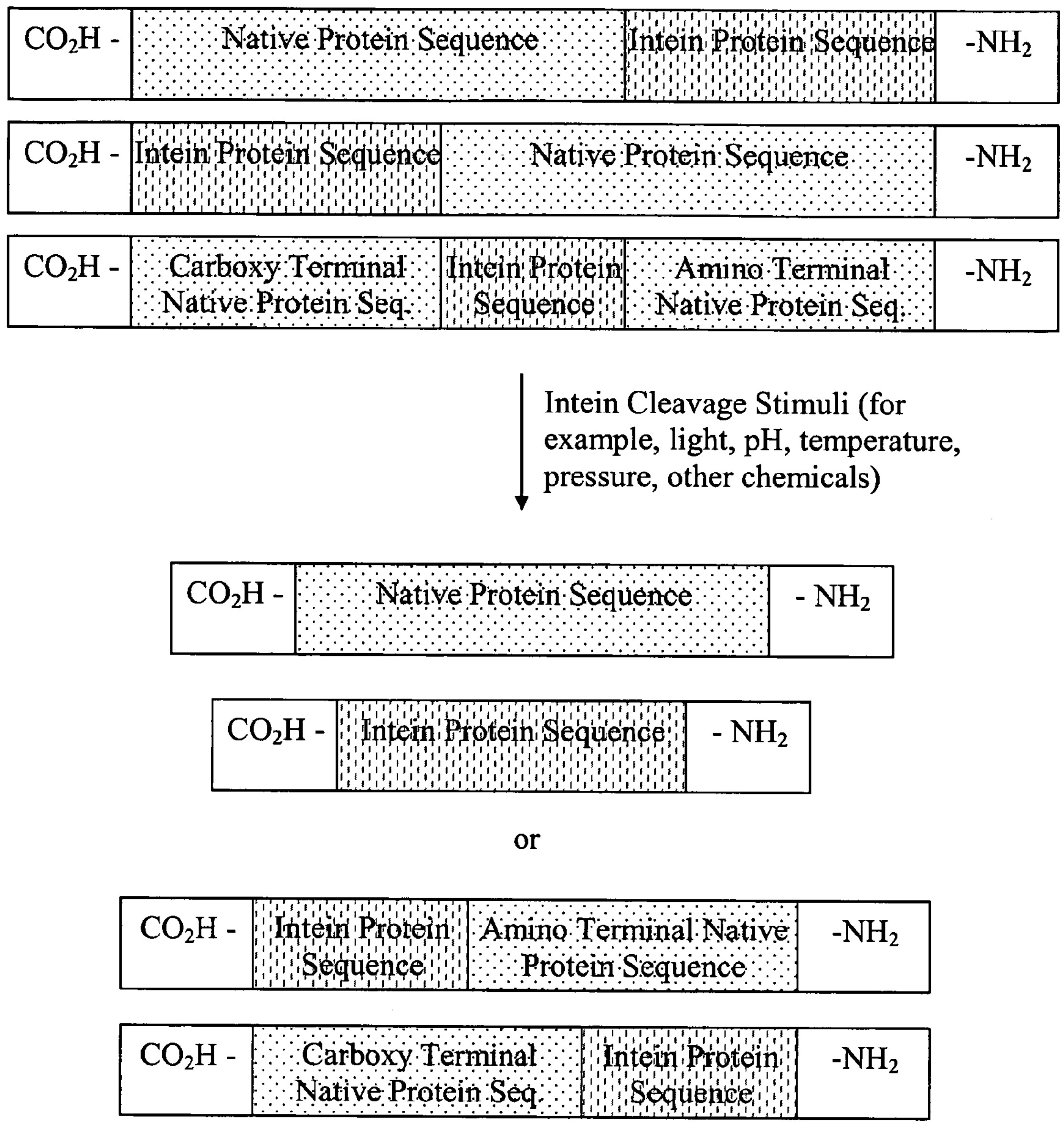

FIG. 3 illustrates the cleavage of an CIVPS or intein modified protein, or components thereof, which may be attained in vitro or in vivo when subjected to an appropriate cleavage stimulus(i). Illustrated here schematically is an example of the cleavage process for a single CIVPS or intein modified protein. Other variants may be constructed as combinations of the CIVPS or intein modified proteins shown in this figure.

DETAILED DESCRIPTION OF THE PREFERRED EMBODIMENT(S)

This invention arose from a desire by the inventor to provide novel methods for generating valuable products from renewable resources, e. g. plant materials or biomass, and to do this in a cost effective manner. One way to effectively attain this goal is by modifying plant biomass through the use of CIVPS or intein modified proteins, where the CIVPS or intein is attached to a desired protein. Within the text of this patent the terms CIVPS and intein are intended to refer to similar products, and will be used interchangeably. From the knowledge that intein modified proteins may be expressed in cells at high titer, yet with substantially decreased activity, he concluded that, if cloned into a plant, this decrease in activity would allow the thus formed transgenic plant cells, plant fragments, or plant tissues, to develop into intein modified protein producing complete plants. Moreover, he thought that such transgenic plants could be provided as several different embodiments, such as those where the recombinant plants are made to express the modified proteins either 1) constitutively or transiently, 2) through chemical induction or biological induction by the plant's growth cycle, 3) throughout the entire plant or specifically in distinct plant tissues, and/or 4) with or without subcellular localization, among others. As envisioned by the inventor, in one embodiment of this invention, the expressed intein modified protein(s) is(are) comprised of a parent protein sequence(s), whose activity(ies) may be known, inferred through sequence or structure homology and/or produced by mutagenesis or by de novo synthesis; each parent sequence(s) being interrupted by, or fused to, an intein sequence(s) or portions thereof. Once inserted, the intein portion(s) of the modified protein(s) inactivate(s), in vivo, the activity or structural utility of the parent protein. The parent protein's original activity may be, however, substantially recovered, if and when desired, by induction of intein splicing. For example, in one application, following plant harvest and during substrate pretreatment, each CIVPS may be induced to splice itself from its parent protein sequence, which parent protein now has recovered its original activity. Methods for intein splicing with, or without, recombining of the protein to a functioning activity are known to one skilled in the art, and need not be repeated here. These methods include the use of light, temperature, change in pH, and/or the addition of chemical reagents.

More specifically, this invention is directed to a recombinant plant, or plant part, plantlet, tissue, cell, sub-cellular fraction, seed, seedling, protoplast, progeny or descendent, comprising an expression construct(s) that encode(s) at least one modified protein comprising a target protein(s) or protein segment(s), which is(are) fused, either internally or terminally, to a controllable intervening protein sequence(s) (CIVPS) or intein sequence(s) or segment(s) thereof, or to an amino terminus(i) or a carboxyl terminus(i) thereof. In one embodiment, each expression construct of the plant, or plant part, plantlet, tissue, cell, sub-cellular fraction, seed, seedling, protoplast, progeny or descendent comprises, operatively linked to one another, a first nucleic acid segment(s) encoding a target protein(s), and a second nucleic acid segment(s) encoding a CIVPS or intein sequence(s), and optionally a selectable marker(s) or reporter gene(s) and/or a promoter(s). It is understood that in a more specific embodiment the sequences may be fused, either directly or via a linker(s), and more preferably in reading frame. The modified protein(s) may be expressed by the plant, or plant part, plantlet, tissue, cell, sub-cellular fraction, seed, seedling, protoplast, progeny or descendent either constitutively, or inductively. In the latter case, the expression and/or splicing of the at least one modified protein(s) may be triggered or induced by a stimulus(i). Examples of suitable stimuli comprise a pH change, change in osmolality, or temperature, the addition of a fertilizer, pesticide, or chemical, or a change in light, and/or sound. The plant, or plant part, plantlet, tissue, cell, sub-cellular fraction, seed, seedling, protoplast, progeny or descendent may express the modified protein(s) either at a pre-determined point of the plant life cycle, in one or more specific tissues or parts thereof, and/or in at least one specific sub-cellular compartment(s). Alternatively or in conjunction with the latter the modified protein(s) may be expressed and secreted extracellularly. The plant, or plant part, plantlet, tissue, cell, sub-cellular fraction, seed, seedling, protoplast, progeny or descendent specific tissue(s) may be seeds, roots, fruits, stems, tubers and/or leaves, and the specific subcellular compartments may be a cellular apoplast, cytosol, chloroplast, plastid, endoplasmic reticulum, inclusion body, vacuole and/or nucleus. Other variations, however, are also included within the confines of this invention.

The plant, or plant part, plantlet, tissue, cell, sub-cellular fraction, seed, seedling, protoplast, progeny or descendent may also carry a selectable marker that confers it resistance to a chemical. Examples of these are bromoxynil, 2,2-dichloropropionic acid, G418, glyphosphate, haloxyfop, hygromycin, imidazoline, kanamycin, methotrexate, neomycin, phosphinothricin, sethoxydim, 2,2-dichloropropionic acid, glyphosphate, hygromycin, trichothecne, sulfonylurea, s-triazine, and/or triazolopyrimidine. Others, however, may also be employed. The promoter may be included to precede a CIVPS or intein-modified protein polynucleotide. In some cases, the plant, or plant part, plantlet, tissue, cell, sub-cellular fraction, seed, seedling, protoplast, progeny or descendent may be tolerant or resistant to normally extremely toxic levels of a selected chemical(s). In another embodiment, the plant, or plant part, plantlet, tissue, cell, subcellular fraction, seed, seedling, protoplast, progeny or descendent is fertile, and has at least one heritable modified protein encoding polynucleotide sequence(s). However, it may just as well not be fertile. Further, as indicated above, also part of this invention are inbred and hybrid genetically recombinant plants, or plant parts, plantlets, tissues, cells, sub-cellular fractions, seeds, seedlings, protoplasts, progeny and descendents, which may or may not be produced by the method of this invention. Of particular interest are plant parts, plant seeds, plant seedlings and plant protoplasts, which have substantial commercial importance. Also of commercial and other interest are plants, plant tissues, plant cells, and sub-cellular fractions. The spliced protein may have the ability of changing the content or activity of one or more plant component(s). In one example, the content may be altered, e.g. reduced, of a plant component such as glucose, fructose, cellulose, hemicellulose, lignin, glycerol, glycine-betaine, pectin, sucrose, lactose, maltose, galactose, amino acids, lipids, vitamins and/or starch, and the like. In another, the plant component whose activity is altered, e.g. reduced, may be one or more of proteins, RNA, and/or lipids, among others. In one aspect, the CIVPS or intein sequence and the target protein or protein segment form at least one splice junction with the target protein. In a desirable embodiment, the amino acid residue at the carboxyl terminus(i) of the splice junction(s) is(are) provided with a hydroxyl or a sulfhydryl side chain(s). In another particularly useful embodiment, the splice junction(s) is placed downstream of the CIVPS or intein sequence(s) or segment(s) thereof, and may comprise(s) an amino acid residue(s) lacking, for example, hydroxyl or sulfhydryl side chains at the amino terminus(i) of the target protein or protein segment(s). In another important variation, the splice junction(s) is(are) placed upstream of the CIVPS or intein sequence(s) or segment(s) thereof, and may comprise an amino acid residue(s) having hydroxyl or sulfhydryl side chains at the amino terminus(i) of the CIVPS or intein sequence(s) or segment(s) thereof. Another important possibility is that where the splice junction(s) is(are) placed upstream of the CIVPS or intein sequence(s) or segment(s) thereof, and it may comprise(s) a cysteine. Still another important variation is that wherein the splice junction(s) is(are) placed downstream of the CIVPS or intein sequence(s) or segment(s) thereof, and may be provided with His-Asn at the carboxyl terminus(i) of the CIVPS or intein sequence(s) or segment(s) thereof, and/or with an amino acid residue(s) having hydroxyl or sulfhydryl side chains at the amino terminus(i) of the adjoining region(s) of the target protein(s). In yet another interesting variant, the splice junction(s) is placed downstream of the CIVPS or intein sequence(s) or protein segment(s) thereof, and may be provided with an Asp at the carboxyl terminus(i) of the CIVPS or intein sequence(s) or segment(s) thereof, and/or with an amino acid residue(s) having hydroxyl or sulfhydryl side chains at the amino terminus(i) of the adjoining region(s) of the target protein(s) or protein segment(s). Further modifications are those where the Asp at the carboxyl terminus(i) is replaced by an amino acid(s) lacking carboxyl or amino side chains, and where the CIVPS or intein sequence(s) or its segment(s) comprise(s) an externally controllable CIVPS or intein sequence(s) or segment(s) thereof, which may be from, among other species, a *Saccharomyces* fungi, and more specifically a *Saccharomyces cerevisiae* fungi. Other constructs suitable for insertion in the products of the invention are those where the CIVPS or intein sequence(s) or segment(s) thereof is(are) inserted immediately before Ser, Thr or Cys of the target protein(s) or protein segment(s), and where the CIVPS or intein amino or carboxy terminus(s) comprise(s) Ser, Thr or Cys, among others. As described in more detail below, the target protein may be expressed in a microorganism, such as a bacterium, as is known in the art. Examples of microorganisms that may be employed are *Bacillus thuringiensis*, or *Phytolacca insularis*. One preferred target protein is *Bacillus thuringensis* endotoxin, which results in a modified *Bacillus thuringiensis* endotoxin being expressed. Another embodiment includes the expression of a target protein from a virus. Although any virus could be employed, examples are potato virus Y, geminivirus, aspermy virus 2b, and cucumber mosaic virus, among others. Another embodiment includes the expression of human target proteins. Although any human protein could be used, examples of preferred proteins include insulin, erythropoietin, growth hormone, tumor necrosis factor receptor, leptin, and other proteins of therapeutic value.

The recombinant plant, or plant part, plantlet, tissue, cell, sub-cellular fraction, seed, seedling, protoplast, progeny or descendent may be produced by a method comprising providing an expression construct that encode(s) at least one modified protein comprising a target protein, or protein segment(s), which is(are) fused, either internally or terminally, to a CIVPS or intein sequence(s) or segment(s) thereof, or to an amino terminus(i) or a carboxyl terminus(i) thereof;

transforming a plant, or plant part, plantlet, tissue, cell, sub-cellular fraction, seed, seedling, protoplast, progeny or descendent, with the expression construct; and regenerating a genetically recombinant plant, or plant part, plantlet, tissue, cell, sub-cellular fraction, seed, seedling, protoplast, progeny or descendent, from the transformed plant, or plant part, plantlet, tissue, cell, sub-cellular fraction, seed, seedling, protoplast, progeny or descendent, that encode(s) at least one modified protein sequence(s).

It is highly preferred that the transformation be a stable transformation. However, transformations that have some temporary stability are also desirable. The regeneration step may be conducted by breeding of a recombinant plant, or plant part, plantlet, tissue, cell, sub-cellular fraction, seed, seedling protoplast, progeny or descendent; crossing of a recombinant plant, or plant part, plantlet, tissue, cell, sub-cellular fraction, seed, seedling, protoplast, progeny or descendent and a non-genetically recombinant plant, or plant part, plantlet, tissue, cell, sub-cellular fraction, seed, seedling, protoplast, progeny or descendent; and/or back-crossing of two genetically recombinant plant, or plant part, plantlet, tissue, cell, sub-cellular fraction, seed, seedling, protoplast, progeny or descendent. The expression construct employed in this method may comprise one or more of promoter, selectable marker, resistance marker, heritable marker, poly-adenylation sequence, repressor, enhancer, localization sequence, and/or signaling sequence. These are intended for use in the application of recombinant technologies as is known in the art, and exemplified elsewhere and below in the examples. In an important aspect of the method, the plant, or plant part, plantlet, tissue, cell, sub-cellular fraction, seed, seedling, protoplast, progeny or descendent is(are) transformed with the expression construct by either viral transformation, bombardment with DNA-coated microprojectiles, liposomal gene transformation, bacterial gene transfer, electroporation, or chemical gene transformation, or more than one of these. As indicated above, the plant, or plant part, plantlet, tissue, cell, sub-cellular fraction, seed, seedling, protoplast, progeny or descendent, may be transformed by means of a bacterium, e. g. *Agrobacterium tumefaciens*, although other microorganisms may also be employed. In the present method, the transformation may be conducted by chemical gene transformation, and it may be done with the aid of, e.g. calcium phosphate, and/or polyethylene glycol, or other chemicals known in the art as being suitable for this purpose. The selection may be attained with the aid of a selectable marker, or a resistance marker, or of the expression of at least one nucleic acid encoding an CIVPS or intein modified protein. In the method of the invention, the genetically recombinant plant, or plant part, plantlet, tissue, cell, sub-cellular fraction, seed, seedling, protoplast, progeny or descendent may be regenerated from a transformed embryogenic tissue(s); plant protoplasts; cells derived from immature embryos; or from transformed seeds, among other sources.

Another method is also provided in this patent, which method is suitable for producing a modified protein(s) or protein segment(s) from a recombinant transformed plant, or plant part, plantlet, tissue, cell, sub-cellular fraction, seed, seedling, protoplast, progeny or descendent expressing the protein(s) or protein segment(s), that comprises conducting the method described above, and further harvesting the modified protein(s) or protein segment(s) from the transformed plant, or plant part, plantlet, tissue, cell, sub-cellular fraction, seed, seedling, protoplast, progeny or descendent. The method may further comprise purifying the modified protein, which may be done by one of many techniques known in the art. As described here, this method may produce a modified protein(s) or protein segment(s) that comprises a CIVPS or intein modified protein(s) or protein segment(s).

Still a further method is provided here for producing a modified protein comprising a target protein(s) or protein segment(s) fused, either internally or terminally, to a CIVPS or intein sequence(s0 or segment(s) thereof, or to its amino terminus(i) or carboxyl terminus(i), which method comprises obtaining an expression construct encoding a target protein having an in-frame fused CIVPS or intein sequence(s) or segment(s) thereof, or its amino terminus(i) or carboxyl terminus(i);

transforming a host plant cell(s) with the expression construct; and culturing the transformed plant host cell under conditions effective for expressing the modified protein.

In one preferred aspect, in the expression construct the at least one first nucleic acid segment(s) encoding the CIVPS or intein sequence(s) or segment(s) thereof is(are) fused to the 5'-end of the second nucleic acid segment(s) encoding the target protein(s) or protein segment(s). Alternatively, in the expression construct the first nucleic acid segment(s) encoding the CIVPS or intein sequence(s) or segment(s) thereof may be fused to the 3'-end of the second nucleic acid segment(s) encoding the target protein(s) or protein segment(s). It is particularly suitable to practice the present method to employ a *Saccharomyces* CIVPS or intein sequence(s) or segment(s) thereof, which is known to effect, either in cis or in trans, excision, cleavage, ligation, excision-ligation, cleavage-ligation, and/or cyclization. When the CIVPS or intein or its(their) segment(s) are employed to induce protein splicing, this event may be induced or triggered by a change of temperature, light or pH, the addition/removal of a chemical reagent that facilitates/inhibits splicing or cleavage, amino acid dephosphorylation or deglycosylation, or by contact with, or removal of, a peptide or peptidomimetic activating or blocking of splicing or of cleavage. Another manner of inducing protein splicing is either in vitro or in vivo contact with, or removal of, a peptide or peptidomimetic agent that may either activate or block splicing or cleavage. Interesting variations that produce superior results are those where the amino or carboxy terminus(i) of the CIVPS or intein sequence(s) or segment(s) thereof comprise(s) Ser, Thr or Cys, or where the carboxyl terminus(i) of the CIVPS or intein sequence(s) or segment(s) thereof comprise(s) Asp preceding Ser, Thr or Cys of the target protein(s) or protein segment(s). However, other modifications are also possible, as is known in the art. See, for example, U.S. Pat. No. 5,834,247 that discloses for the prokaryotic and eukaryotic realms some methodology incorporated in this invention to the production of hybrid plants of useful characteristics. In the present method, the expression construct may further comprise a promoter, a selectable marker, a resistance marker, a heritable marker, a poly-adenylation sequence, a repressor, an enhancer, a localization sequence, or a signaling sequence. Moreover, the method presented here may also comprise the transformation of the plant, or plant part, plantlet, tissue, cell, sub-cellular fraction, seed, seedling, protoplast, progeny or descendent with the expression construct being implemented by viral transformation, bombardment with DNA-coated microprojectiles, liposomal gene transfer, bacterial gene transfer, electroporation, and/or chemical gene transformation, and/or other methods known in the art, or that will be subsequently developed. As described above, in the method described here, the bacterium used to transfer the expression construct may be an *Agrobacterium tumefaciens* bacterium; the chemical used for transformation may be calcium phosphate, or polyethylene glycol; the transformed plant cells, plant parts, plants, etc. may be selected through their expression of a selectable marker, or resistance marker; the selection of the transformed plant, or plant part, plantlet, tissue, cell, sub-cellular fraction, seed, seedling, protoplast, progeny or descendent may be conducted through their expression of the modified protein gene sequence; and the regeneration of the genetically recombinant plant, or plant part, plantlet, tissue, cell, sub-cellular fraction, seed, seedling, protoplast, progeny or descendent may be attained from transformed embryogenic tissue; from cells derived from immature embryos; or from transformed seeds, among others.

Also disclosed in this patent is a method for producing seed that express a modified protein(s), this method comprising obtaining the genetically recombinant plant, or plant part, plantlet, tissue, cell, sub-cellular fraction, seed, seedling, protoplast, progeny or descendent of the invention;

culturing or cultivating the genetically recombinant plant, or plant part, plantlet, tissue, cell, sub-cellular fraction, seed, seedling, protoplast, progeny or descendent; and obtaining from the cultivated plant seed that expresses a modified protein(s).

Still another method provided by this patent is one for using a plant, or plant part, plantlet, tissue, cell, sub-cellular fraction, seed, seedling, protoplast, progeny or descendent expressing a modified protein for producing a compound, the method comprising harvesting a recombinant plant, or plant part, plantlet, tissue, cell, sub-cellular fraction, seed, seedling, protoplast, progeny or descendent in accordance with the teachings of this patent;

mechanically processing the plant, or plant part, plantlet, tissue, cell, sub-cellular fraction, seed, seedling, protoplast, progeny or descendent;

combining the mechanically processed plant, or plant part, plantlet, tissue, cell, sub-cellular fraction, seed, seedling, protoplast, progeny or descendent, with a non-genetically recombinant plant in a proportion greater than or equal to zero recombinant:non-recombinant; and chemically processing the plant or specific portions of the plant under conditions effective for obtaining the compound.

This method may be practiced by mechanical processing of the plant, or plant part, plantlet, tissue, cell, sub-cellular fraction, seed, seedling, protoplast, progeny or descendent by extrusion, grinding, shredding, mulching, chipping, dicing, compressing, exploding, and/or tearing. Other processing techniques, however, are also suitable. The chemical processing of the combined components may be attained by various techniques or a combination thereof. Some of them are pre-treatment with steam, dilute or concentrated acid, ammonia explosion, sterilization, soaking in water, mixing with a solvent, a change of pH, temperature or osmolality, exposure to or changes in light, inorganic and/or enzyme catalysis, saccharification, bleaching, scouring, fermentation, distillation, chromatography, adsorption, and/or addition of a chemical(s). Others, of course, are also employed successfully. Various steps are of use when practiced as follows: the pre-treatment may include steaming the combined products for sterilization purposes; the chemical processing may be attained by pre-treatment with at least one of sulfuric acid, hydrochloric acid, phosphoric acid, or carbonic acid, or by soaking in water at a temperature greater than or equal to about 20° C., and/or by mixing the combined products with at least one of water, or an organic or inorganic solvent(s). As already explained, an external stimulus(i) may be applied to induce splicing of the modified protein(s) or protein segment(s). Examples of external stimuli are a change of pH, osmolality, or temperature, exposure to sound, light, or addition of a chemical(s). In some cases the spliced protein(s) or protein segment(s) may exhibit altered activity(ies) with respect to the modified protein(s) or protein segment(s), such as altered binding, catabolic or anabolic activity(ies) with respect to the original target protein(s). Examples of spliced protein(s) or protein segment(s) are those capable of degrading starch, dextrin, pectin, lipids, protein, chitin, lignin, cellulose, or hemicellulose, or modifying lignin, or having saccharification activity. Thus, the spliced protein may be capable of producing glucose, fructose, xylose, phenol, glycerol, mannose, lactic acid, acetic acid, ethylene, propylene, toluene, ethyl benzene, styrene, xylene, ethylene glycol, butadiene, formaldehyde, isopropanol, acetone, butanediol, methanol, ethanol, propanol, butanol, propanediol, vitamins, methane, ethane, propane, butane, pentane, hexane, heptane, octane, benzene, target proteins, therapeutic proteins, enzymes and/or biopolymers, among other compounds. In one specific embodiment of the pre-treatment, saccharification, and fermentation may be conducted in one step, and the fermentation may be attained by employing a prokaryotic or eukaryotic microorganism capable of producing lactic acid, acetic acid, ethylene, propylene, toluene, ethyl benzene, styrene, xylene, ethylene glycol, butadiene, formaldehyde, isopropanol, acetone, butanediol, methanol, ethanol, propanol, butanol, octanol, propanediol, vitamins, methane, ethane, propane, butane, pentane, hexane, heptane, octane, benzene, and/or biopolymers, among other compounds.

This invention also encompasses the production of animal feedstock that comprises a nutritious amount of the recombinant plant, or plant part, plantlet, tissue, cell, sub-cellular fraction, seed, seedling, protoplast, progeny or descendent of the invention. When the feedstock provided by the inventor is ingested by an animal, the modified protein(s) or protein segment(s) is(are) spliced by an internal stimulus(i) from the animal. Examples of internal stimuli are the animal's saliva, bile, chymotrypsin, trypsin, bicarbonate, hydrochloric acid, or stomach pH or temperature, among others. The feedstock of the invention may comprise spliced protein(s) such as phytases, endocellulases, exocellulases, amylases, glucanases, hemi-cellulases, pectinases, proteases, xylanases, or lipases, growth factors or a growth hormone. Other proteins, however, could also be employed as desired.

Yet another aspect of this invention provides for the use of the feedstock described above in the manufacture of an immune response enhancing composition, wherein the spliced protein(s) or protein segment(s) comprise(s) at least one recombinant immunogen(s). The immunogen may included one or more viral or bacterial immunogens, and it may be formulated in various suitable forms. Preferred are an oral formulation, a trans-mucosal formulation, a gastrointestinal (G.I.) tract absorbed formulation. However, this composition of matter may be formulated in any systemic or topical form suitable for administration to an animal, including its addition to animal feed.

The animal feedstock of the invention may be produced by first conducting the steps indicated above to obtain a genetically recombinant plant, or plant part, plantlet, tissue, cell, sub-cellular fraction, seed, seedling, protoplast, progeny or descendent, and then processing the genetically modified plant, or a portion of the resulting product under conditions effective to obtain an animal digestible feedstock.

The product of this invention may also be employed for promoting animal growth, for example by producing feedstock that comprises a growth promoting product, and allowing an animal access to the modified feedstock. The product of this invention may also be employed for enhancing an animals immune response. This may be done by administering to an animal in need of the treatment, an immune enhancing amount of the composition of the invention.

A further aspect of this invention involves a method for producing a target protein(s) or protein segment(s), the method comprising producing a first modified protein(s) or protein segment(s), wherein the amino terminus of a CIVPS or intein sequence(s) or segment(s) thereof is(are) fused to the carboxyl terminus(i) of a target protein(s) or protein segment(s) by the method described above;

producing a second modified protein(s) comprising a segment(s) of the CIVPS or intein sequence(s); and contacting first and second modified proteins under conditions effective for trans cleavage of the CIVPS or intein sequence(s) or segment(s) thereof by the second modified protein(s).

Yet another variation of the above method for producing a target protein(s), comprises producing a first modified protein(s), wherein the carboxyl terminus of a CIVPS or intein sequence(s) or protein segment(s) thereof is(are) fused to the amino terminus(i) of the target protein(s) or protein segment(s) by the already described method;

similarly producing a second modified protein(s) or protein segment(s) comprising a segment(s) of the CIVPS or intein sequence(s); and contacting first and second modified proteins under conditions effective for trans cleaving the CIVPS or intein sequence(s) or segment(s) thereof from the first modified protein(s) or protein segment(s). The cleavage may be induced in this procedure by a change in temperature, light, or pH, addition/removal of chemical that facilitates/inhibits splicing or blocking of cleavage, amino acid dephosphorylation or deglycosylation, and/or contact/removal of peptide or peptidomimetic that activates/blocks splicing/cleavage, among others.

Thus, the invention is directed towards transgenic plants, which term is intended in this patent to be synonymous with genetically recombinant plants, their seeds and progeny plants, or any plant portion, tissue or cell, containing a gene(s) for an CIVPS or intein modified protein(s). The invention is further directed towards methods for the production of the transgenic plants that produce CIVPS or intein modified proteins, methods for the production of CIVPS or intein modified proteins in plants, and uses of the plants as substrates for fuels, chemicals, animal food or food additives, paper, and pharmaceutical production. The invention allows for the production of transgenic plants that can be used as a source of binding, structural or catalytic components, or can have their intein modified proteins purified and used separately as binding, structural or catalytic proteins. Transgenic plants are multi-cellular plants that express single or multiple exogenous genes and their associated protein (or ribonucleic acid) activities. Within the context of this invention, gene or enzyme classes may be specifically referred to, however this is not a limiting aspect of the invention. When specific classes are stated, this is understood to identify any gene or enzyme within the specific classification. CIVPS or inteins are protein sequences internal or adjacent to a parent protein sequence, that may spontaneously cleave themselves at either, or both, the carboxyl or amino terminal ends and are capable of selectively ligating the resulting extein protein fragments when appropriate, under specific conditions. See, for example, Perler, et al., Nucl. Acids Res., 22:1125-1127 (1994); Wallace, C. J., Protein Sci., 2:697-705 (1993); Xu, et al., Cell, 75: 1371-1377 (1993); Pietrokovski, S., Protein Sci., 2:697-705 (1994). Thus, CIVPSs may be said to be in-frame, self-cleaving peptides that generally occur as part of a larger precursor protein molecule. CIVPS or inteins differ from other proteases or zymogens in several fundamental ways. Unlike proteases that cleave themselves or other proteins into multiple, unligated polypeptides, inteins have the ability to both cleave and ligate in either cis or trans conformations. Thus as opposed to terminal cleavage that would result from the reaction of a protease on a protein, inteins have the ability to cleave at multiple sites, and ligate the resulting protein fragments. This cleavage is induced under specific conditions and may be brought about implementing techniques that are known in molecular biology. Inteins from various sources, their sequences, characteristics and functions have been described fully in the literature. See, for example, Kane et. al., Science 250:651 (1990); Hirata et al., J. Bio. Chem. 265:6726 (1990) (*Sacchromyces cerevisiae*); Davis et al., J. Bact. 173: 5653 (1991), Davis et al., Cell 71:1 (1992) (*Mycobacterium tuberculosis*); Perler, et al., PNAS 89:5577 (1992) (*Thermococcus litoralis*). As shown in FIG. 1, the combination of an CIVPS with a protein of purported activity or structural role yields an intein modified protein, whose purported activity or structural role may be substantially altered. Transgenic plants that express CIVPS modified proteins (from their associated intein modified genes) are an improvement upon previous transgenic plants, because the parent intein modified protein can have two substantially different states that are controllably mediated by intein cleavage. This cleavage may or may not be associated with recombination of the purported protein sequence. The invention may be formed from any plant species, combined with any combination of single or multiple proteins and CIVPS. Plant species may include, but are not limited to: poplar, birch, cedar, pine, hardwoods, softwoods, soybeans, switchgrass, corn, tobacco, alfalfa, sugar cane, cauliflowers, artichokes, bananas, apples, cherries, cranberries, cucumbers, lettuce, grapes, lemons, melons, nuts, tangerines, rice, oranges, peaches, pears, blueberries, strawberries, tomatoes, carrots, cabbages, potatoes, endive, leeks, spinach, weeds, arrowroot, beets, carrots, cassava, turnips, yams, radishes, sweet potatoes, wheat, barley, soya, beans, rapeseed, millet, sunflower, oats, peas, tubers, bamboo, seaweed, algae, or any other plant species. Proteins may include any known, putative, modified, or de novo created proteins. Although the selection of the native protein is not restricted, preferred proteins include lignocellulosic degrading proteins (cellulases, lignases), starch degrading enzymes (amylases, glucanases), enzymes in the biosynthetic pathways required for fuel or chemical production, bacterial or viral antigens, enzymes in the biosynthetic pathways for vitamins or other food additives (phytases, cellulases, amylases, glucanases, hemi-cellulase, pectinase, protease, xylanase, lipase, growth hormone), proteins that impart pest or insect resistance, proteins that impart herbicide resistance, and therapeutic proteins (insulin, erythropoietin, growth hormone, leptin, tissue plasminogen activator, tumor necrosis factor receptor, Her2 receptor) implicated in disease pathogenesis. The choice of CIVPS or intein used to modify the protein, the fusion of which is expressed in the desired plant, is also not limited. Any single or multiple CIVPS or intein may be used in any configuration with respect to the desired protein or proteins. The CIVPS or inteins should have the capability to be spliced at one or both ends in response to some stimuli, and may or may not permit ligation of the proteins to which single or multiple CIVPS or inteins are fused.

Transgenic plants expressing CIVPS or intein modified proteins, and the production of CIVPS or intein modified proteins in transgenic plants can be accomplished by combining methods (Ausubel, et al.) known in the art. Generally, these methods include construction of a DNA containing the CIVPS or intein modified protein of interest and the necessary regulatory elements required for its expression, amplification and selection of the constructed DNA, transformation of the desired plant species, regeneration and selection of the appropriately transformed plant species, and if necessary, purification of the CIVPS or intein modified protein in its native form or the cleaved form. Both the production of transgenic plants expressing CIVPS or intein modified proteins, and the production of CIVPS or intein modified proteins in transgenic plants form part of this invention. For the production of the transgenic plants, or CIVPS or intein modified proteins in transgenic plants, the CIVPS or intein modified protein DNA sequence must be constructed. This is easily accomplished by cloning the gene sequence of the desired activity and the desired intein sequence into *E. coli* or any other suitable host (e.g., yeast may be beneficial in some cases, or expression in mammalian or plant cells with or without the use of viral or non-viral vectors). Once the gene and intein coding sequences have been cloned, they must be joined in the desired configuration. The chosen intein sequence should be able to perform the desired functions such as splicing in response to an imposed stimuli (for example, light, pH change, temperature, pressure, or changes in the local chemical composition surrounding the intein modified protein), and if necessary permitting ligation of the fused protein. Joining of the CIVPS or intein's DNA sequence and the protein's DNA sequence is easily accomplished by methods known in the art, resulting in CIVPS or intein modified protein DNA coding sequences, or combinations thereof, as shown in FIG. 1. As already indicated, an CIVPS or intein modified protein is one which fuses the CIVPS or intein to one of either the carboxy terminal, amino terminal, or internal portions of the native protein or proteins. Although many alternative methods exist, one way of creating the fusion between the CIVPS or intein and desired protein coding sequences would be to purify the DNA encoding the desired protein sequence, use a restriction enzyme to cut the protein coding sequence at the desired point of intein insertion, and then ligate the intein coding sequence into the restricted site. The polynucleotide, or either of the nucleic acid segments may be cloned directly to appropriate regulatory and/or selection sequences, or via a vector them. Examples of regulatory segments are promoters to control the temporal expression of the CIVPS or intein-modified protein, origins of replication, and/or signaling sequences to control the spatial distribution of CIVPS or intein-modified proteins in vivo in specific plant tissues and/or specific subcellular compartments, and/examples of selection elements are herbicidal or antibacterial genes, fluorescent makers, dye markers, and other suitable selective markers. The resulting polynucleotide or vector comprising the CIVPS or intein modified protein(s) encoding polynucleotide(s), and optionally any desired regulatory, and selection elements, then may be amplified to obtain larger amounts of product, which may be used for subsequent transformation of a desired plant species. Modification of any and all of these steps is possible to facilitate specific orientation and fusion between any desired CIVPS or intein(s) and protein(s) polynucleotides, and it is conducted employing methods that are known in the art. Alteration of either the coding sequences and/or the CIVPS or intein coding sequence and the ligation of either or both of these sequences may also be easily accomplished by techniques known in the art, such as site-directed mutagenesis, codon optimization, random mutagenesis, polymerase chain reaction (PCR), error-prone PCR, and/or any other suitable method that would be considered routine by an artisan. These techniques facilitate the placement of a number of joining sequences, and any desirable and suitable combination may be used. Likewise, any combination or orientation of regulatory and selective elements may also be implemented in accordance with this invention. Gene regulatory elements, such as promoters (Guilley et al., Higgins, T. J. V., Coruzzi et al., Tingey et al., Ryan et al., Rocha-Sosa et al., Wenzler et al., Bird et al.), enhancers (Brederode, et al.), RNA splicing sites, ribosomal binding sites, glycosylation sites, protein splicing sites, subcellular signalling sequences (Smeekens et al., van den Broeck et al., Schreier et al., Tague et al.), secretory signal sequences (Von Heijne, G., Sijmons, et al.), or others may be advantageous in controlling either the temporal or spatial distribution of the CIVPS or intein modified protein concentration and activity in vivo in the transformed plant. Use of these elements may be desired to facilitate the production and processing of intein modified proteins in transgenic plants. The expression of the intein-modified protein(s) may be conducted either in a constitutive or induced manner. In order to attain either of these modes, any of the methods that are either described in this patent or known in the art, or later made available, may be implemented. The induction of protein expression may be attained with the aid of a foreign stimulus (i). Examples of these are the exposure to a pesticide(s), to light, a temperature change(s), and/or sound(s). Other foreign stimuli, however, may also be employed. In addition, the recombinant plant may also express any one or more of the selectable marker gene or reporter gene(s) mentioned above.

Once the CIVPS or intein modified protein DNA sequence has been constructed, optionally codon optimized, combined with the desired regulatory and selection DNA sequences, successfully cloned and selected, then transformation of the desired plant species and generation of full plants is required. Methods for transformation of a desired plant species, and the generation of full plants can be accomplished by techniques known in the art (Draper, et al., Potrykus, et al.). Transformation techniques include, but are not limited to: *Agrobacterium tumefaciens* mediated gene transfer, *Agrobacterium rhizogenes* mediated gene transfer, direct gene transfer to plant protoplasts, Ti plasmid mediated gene transfer (with or without a helper plasmid), biolistic or particle bombardment plant transformation (Gordon-Kamm et al.), microinjection and fiber-mediated transformation, and tissue electroporation (Shimamoto et al.). Gene transfer may occur in whole plants, plant explants (such as, but not limited to root explants), any plant portion (such as, but not limited to plant leaf segments, seeds, or seed segments), plant protoplasts or apoplasts, or single or multiple plant cells. Each different method has been substantially described in detail by the prior art. Methods of selection of properly transformed plants are known in the art. Selection methods may be facilitated by including a selectable marker in the transformed DNA containing the CIVPS or intein modified protein (such as a resistance gene, gene coding the production of a colored compound, gene coding the production of a fluorescent compound, or any other suitable method). Additionally, DNA from transformed plants may be isolated and sequenced to confirm the presence of the desired CIVPS or intein modified protein coding sequence. Other techniques are also suitable for confirmation of the selection process, such as polymerase chain reaction, restriction digest analysis and Southern analysis. Any method of selection that allows identification of the desired transgenic plant may be used. Once the plant is transformed with the CIVPS or intein modified protein and desired regulatory and selection sequences, whole plants can be regenerated by methods know to the art (Horsch et al.). Most methods consist of culturing the transformed plant cells, explants, tissues, parts, or whole plants in the proper medium and under appropriate conditions of light and temperature. The method used to regenerate the plant should not limit the invention and any effective method may be used. The resulting transgenic plant should produce CIVPS or intein-modified proteins that are substantially described as, or a combination of, those shown schematically in FIG. 2. Once the whole, transgenic plant has been selected, it can be monitored for CIVPS or intein modified protein expression. This is not required for the production of transgenic plants expressing CIVPS or intein modified proteins, but is prudent to confirm that the desired transgenic plant expressing the desired CIVPS or intein modified protein has been obtained and expression is properly controlled by the desired control elements used. Monitoring of CIVPS or intein modified protein expression is necessary for the purification of the CIVPS or intein modified proteins in the cleaved or uncleaved state, as described schematically in FIG. 3 for either whole intein modified proteins, or components of intein modified proteins that are composed of combinations of elements shown in FIG. 3. Protein expression of the intein modified protein can be monitored by western analysis, 2-dimensional gel electrophoresis (and staining), or mass spectrometry, conducted on plant extracts or protein fractions purified from the transgenic plant. In addition, either some of the purified proteins, or the transgenic plant itself, should be exposed to the intein cleavage stimulus. After exposure, both the CIVPS or intein modified protein and the resulting protein that appears as a consequence of CIVPS or intein cleavage can both be analyzed by western analysis, and other assays, to verify the presence of the appropriate proteins, and the difference in activity between the intein modified protein and the resulting cleaved protein. The activity assays must be designed so as to monitor the desired protein activity and should be specific to that activity and not vulnerable to competing interferences. A control can be used as a standard to compare the native activity with both the intein modified activity and the activity following intein cleavage. Methods and processes using transgenic plants expressing CIVPS or intein modified proteins include the use of the plants as substrates for fuel production (including, but not limited to: burnable biomass, ethanol, methanol, propanol, propane, methane, or octane production), the use of the plants as substrates for commodity chemical production (including, but not limited to: lactic acid, ethanol, glucose or other hexoses, pentoses, propane diols, ethene, ethane, ethylene, phenolic compounds, amino acids, paper pulp, pesticides, insecticides, other alcohols, other ethers, other esters), the use of the plants as substrates for food production and or food additive production (including but not limited to: amino acids, sugars, vitamins, fiber, or cattle feed), the use of the plants for vaccine delivery, the use of the plants for the production of therapeutic proteins (including but not limited to: insulin, erythropoietin, growth hormone, leptin, tumor necrosis factor receptor, glucagon, gamma interferon, or Her2 receptor), the use of the plants for paper production, and the use of the plants for remediation of waste materials. Any batch, semi-batch, or continuous process in which transgenic plants that express intein modified proteins are used as substrates for one of the purposes described above is claimed. These processes may include, but are not limited in scope to, processes in which the transgenic plants expressing intein modified proteins are harvested, exerted to the intein cleavage stimuli, mixed with other substrates in a transgenic plant to substrate ratio greater than or equal to zero, and then converted either chemically, enzymatically, or biologically to one of the products detailed above.

The examples provided below illustrate the process of the invention, as well as the manufacture of transgenic plants expressing CIVPS or intein modified cellulase enzymes, and the thus produced plants. In these plants the cellulase enzymes are expressed as dictated by the regulatory elements controlling the CIVPS or intein modified genes. The cellulase activity is substantially reduced in vivo by interruption of the native cellulase enzyme by the fused intein. This allows the plant to grow, uninhibited or with little inhibition by cellulase activity. The plants may be harvested and exerted to the intein cleavage stimuli, such as exposure to a certain wavelength of light, mixed with a sulfurous or pH altering chemical, mixed with a salt, mixed with any other chemical, or exerted to a change in temperature. In this case, the CIVPSs or intein is be cleaved and the cellulase activity recovered, which then catalyzes the cleavage of cellulose and/or lignin. At this point the cleaved protein plant mash may be mixed in any proportion, preferably greater than or equal to zero, with other plant substrates, chemical substrates, municipal waste, manufacturing by-products, enzymes, and/or prokaryotic or eukaryotic cells, among others, to aid in the conversion of the plant substrate to the desired product, e.g. a fuel, commodity chemical, food for human or animal consumption, food additive, paper pulp, or vaccine antigen, among others. It should also be noted that the use of the present invention is not limited to manufacturing processes or mechanical processes. Non-limiting examples of applications of this invention are in the delivery of vaccines, hormones, or therapeutic proteins, in which case the intein modified protein may comprise a combination of therapeutic protein(s) and/or protein antigen(s), potentially protective protein sequences, and CIVPSs or intein(s) that may be expressed by the transgenic plant, e.g. a banana plant. The delivery process may occur, for example, by ingestion of the plant product by a human or non-human animal. The plant is then masticated in the mouth and exposed to a stimulus(i) in vivo in the stomach, which in turn triggers or induces cleavage by the CIVPS or intein. In the case of humans the stimulus may be the reduced pH of the stomach, which induces the cleavage of the CIVPS or intein from the antigen or therapeutic protein, and provides for appropriate ligation, if necessary. The therapeutic protein or antigen would then flow into the duodenum, or small intestine, where the pH would be neutralized and protein products are now ready to be absorbed into the blood stream.

Background For Exemplary Information Provided Below

Many different variations in the protocol presented in Example 1 below are suitable for practicing the present invention, as an artisan would know. In general, a DNA sequence encoding a CIVPS or intein modified protein is constructed and packaged into an appropriate vector, plant material, whether it is single cells grown in suspension, protoplasts, plant segments or parts, whole plants, or other forms suitably described here are transformed with the vector, and complete plants, seeds, or other plant forms described here are regenerated. Example 1 shows one embodiment of the inventive method, variations of which are possible that may be used to generate a transgenic tree, e.g. a poplar species expressing an intein modified cellulase. The choice of desired protein, however, depends upon the application the transgenic plant species is intended for. In this regard native proteins, de novo synthetic proteins, or evolved proteins, e.g., by gene shuffling, error prone PCR, or any other analogous method, may be used. Cellulases catalyze a cleavage reaction in breaking down cellulose, a chemical component of the plant. While other plants have been constructed expressing cellulases the enzymes typically have to be transiently expressed, or sequestered in parts of the cell so as not to disrupt plant tissue differentiation and development. See, for example, Ziegler et al. (2000); Dai et al. (a), (2000); Dai et al. (b) (2000); Montalvo-Rodriguez et al. (2000). Hence, in the case where the cellulase activity is not controlled by localization or transient expression, whole plants are often very difficult to regenerate, or the cellulase activity is often too low to be useful. By using an intein modified cellulase, the whole plant can be regenerated while the less activate intein modified cellulase is produced throughout the plant and at high titer. See, Aspergen et al., *Molecular Breeding* 1:91-99 (1995). The enzyme can be subsequently activated by the self-splicing ability of the intein to yield a cellulase of increased activity relative to the intein modified cellulase. It is noteworthy that any native protein will meet the requirement for this invention, and selection of the protein is dependent upon the plant's intended purpose. In this case, a poplar species that could be induced to de-polymerize its own cellulose would be beneficial for ethanol production from biomass, or as a substrate for fermentation of other chemicals.

Contruction of CIVPS or Intein Modified Proteins

Various recombinant DNA techniques may be used in combination to construct the vector carrying the DNA encoding the modified protein. One of the easiest and most direct utilizes the polymerase chain reaction (PCR) to assemble the nucleic acid sequence encoding the intein-modified protein with appropriate complementary ends that facilitates ligation into the desired vector. The PCR method is illustrated here. Other methods may be used to accomplish this same goal, and some rely on specific restriction and ligation of the desired protein and intein encoding sequences, but may still include PCR steps. PCR Kits for conducting the reaction are readily available (Epicentre, Madison, Wis.). The only requirements on the primers is that one should match the 5' end of the sense strain to be amplified, and the other should match the 5' end of the corresponding antisense strain; relative sequence uniqueness is beneficial.

Clean-Up and Purification from a Gel

The purification of DNA from a gel may be accomplished using electroelution, phenol extraction, agarase digestion, glass bead extraction, or from a number of commercially available kits. The commercially available QIAquick Gel Extraction Kit (Qiagen, Valencia, Calif.) and associated method is one example.

Selection of Intein According to Intended Use

Two features are of importance in this step: the property the CIVPC or intein possesses to induce splicing that will facilitate optimization of the transgenic plant for its intended purpose, and where to place the intein within the nucleic acid sequence encoding the target protein. Any coding sequence for a self-splicing protein, i.e. an intein, may be used in this invention. A compilation of some known inteins is given in Perler, F. B. (2002). *InBase, the Intein Database. Nucleic Acids Res.* 30, 383-384. Other inteins remain to be discovered and new inteins may be created through sequence analysis, recombinant DNA methods, and mutation of known sequences. This intein of Example 1 is advantageous for the intended transgenic poplar species because upon splicing it yields predominantly ligated, native protein (>75%), and is temperature sensitive so that intein splicing is inhibited at temperatures less than 30° C., and is not substantial until 50° C., at which temperature the half-life of the uncleaved protein is less than 2 hours.

used, depending upon the desired stimulus and mechanism for intein splicing. If desired, the codons at the extein-intein junction may be altered to facilitate these requirements. Care is advised when altering the junction codons, so that the intein modified protein may cleave as desired, and allow the resulting products to perform the appropriate activity. The intein position within the native target protein such is to substantially change the activity of the resulting intein modified protein. In most circumstances virtually any interruption within or near the active site of the molecule meets this criterion. The combination of the amplified intein sequence and the amplified native protein sequence is easily accomplished if a serine residue resides close to a unique restriction site of the native protein's coding sequence. Conversely, the intein coding sequence is readily incorporated at any desired position in the native protein sequence by using several polymerase chain reactions. A preferred PCR method is set forth here. Preferrably 50 oligonucleotide primers are used. Shorter primers may be used, however it is beneficial, although not necessary, to use primers of the same length. The sense primer of the C-extein may hybridize to both the C-extein and intein sequence at the junction to facilitate the fusion of the amplified sequences in subsequent PCR amplifications. For intein amplification, both primers preferably overlap with their respective desired adjacent extein sequences to facilitate fusion of the intein sequence and extein sequences in subsequent PCR amplifications. The polymerase chain reaction is preferably carried out using the standard protocol outlined above, but may have some optimization. Typical optimization parameters are the amount of template and primer DNA added to the mixture (generally the primer DNA is added in great excess relative to the template DNA), the temperatures and times for the reaction cycles, the number of cycles, and the $MgCl_2$ concentration. The length and composition of the primers used may also be varied to yield an effective intein modified protein, so long as the constraints on placement are observed. Kits are commercially available which include all necessary reagents: Taq DNA polymerase, $MgCl_2$, 25 mM dNTP mixture (containing equamolar amounts of dATP, dCTP, dGTP, and dTTP), reaction buffer, and water.

At this point the next round of PCR is started to fuse the extein and intein sequences. In this case the intein fragment is preferably mixed with an equimolar portion of the C-extein cellulase fragment. Combination of these fragments represents both the template and primers (overlapping regions) to be used. Addition of reaction buffer, 25 mM dNTPs, $MgCl_2$, and Taq DNA polymerase is still required, as are the changing temperature cycles. This reaction is preferably augmented by addition of the following sense and anti-sense primers, respectively, along with *E. coli* DNA ligase (New England Biolabs, Beverly, Mass.), however this addition is not necessary and depending upon the exact reaction conditions employed may not lead to an increase in the yield.

```
5'-ACAGAATGGGGAACGAGCGATGCTAGCATTTTACCGGAAGAATGGGTTC-3'   [SEQ ID NO: 1]

5'-CGTGTCTGCTCCGTTTACCGCTTTTTTTAATTGGACGAATTTGTGCGTGA-3'  [SEQ ID NO: 2]
```

Construction of Intein Modified Protein

In order to ensure proper intein splicing, the intein is inserted in Example 1 in frame next to a serine, cysteine, or threonine residue of the native target protein. This leaves the native target protein's serine, cysteine, or threonine on the carboxylic acid side, of this intein's histidine—asparagine, conserved residues at the terminal 536 and 537 intein amino acid positions, respectively. Other terminal residues may be Once completed, the PCR products are preferably again run on an agarose gel, and the appropriate band, 2665 nucleotides long, purified from the gel and analyzed according to the methods described above. A small amount of the purified reaction product is preferably used for quantitation by measuring the absorbance at 260 nm and 280 nm wavelengths on a UV spectrophotometer. To complete assembly a PCR reaction of the intein modified cellulase coding sequence is carried out combining equimolar amounts of the fused C-extein and intein fragments just constructed, with the N-extein fragment purified previously. The PCR reaction is preferably conducted using the same temperature cycles as in the previous reaction after addition of reaction buffer, 25 mM dNTPs, $MgCl_2$, and Taq DNA polymerase. This reaction is preferably augmented by addition of the following sense and anti-sense primers, and *E. coli* DNA ligase (New England Biolabs, Beverly, Mass.); however this addition is not necessary and depending upon the exact reaction conditions employed may not lead to an increase in the yield.

```
5'-AGCATTCAGACCTCCCATTTCATACGAAAAGAGGAAATAGATAGATTTTC-3'  [SEQ ID NO: 3]

5'-CGTGTCTGCTCCGTTTACCGCTTTTTTTAATTGGACGAATTTGTGCGTGA-3'  [SEQ ID NO: 4]
```

Vector Construction

Other elements may be included in the expression cassette prepared in Example 1, e.g. extracellular secretion signaling sequences, intracellular localization signaling sequences, other inducible promoters, etc. As the vector is now contained within the recombinant strain *A. tumefaciens*, the gene transfer to the poplar plant relies on the bacteria's specialized delivery system. Other gene transfer methods are available, and selection of a suitable transformation method depends upon the source of the plant material. For example, protoplasts or individual plant cells may be transformed directly with the recombinant pTiBo542 plasmid using electroploration, calcium chloride, or Biolistic particle bombardment (Bio-Rad, Hercules, Calif.). Conversely plant callus, plant segments, or in some cases, whole plants may be used as starting material, when appropriate. For efficient gene transfer to occur, the time of incubation and cell density of the culture is preferably optimized.

Advantages and Uses for Transgenic Poplar of Example 1

The resulting transgenic poplar species may be grown and passaged indefinitely while producing the intein modified cellulase in high titer. The cellulase may be subsequently activated by harvesting the plant, mechanically chipping or grinding it to increase the exposed surface area, and then incubating the resulting mash in a vat or tank at an elevated temperature (preferably 30° C. to 50° C.) and/or lower pH (6.5 or below). Exposure to the elevated temperature, and lower pH, if used, will induce the intein splicing and yield the native cellulase at a substantially increased activity. Under these conditions the cellulase may now catalyze the cleavage reaction of cellulose to economically produce substrates that may be subsequently fermented into ethanol or other chemical entities. In addition, this plant may be used as a source of either the intein modified cellulase, or the recovered native cellulase, post splicing. In either case, the protein is preferably purified from the plant using methods well known in the prior art, such as precipitation, membrane filtration, chromatography including affinity chromatography, extraction, etc.

The use of transgenic plants producing intein modified proteins has two advantages over previously reported transgenic plants. Because the intein modified protein has substantially less activity than the native protein, it may be expressed at higher titer and localized anywhere in the plant species. Previous reports of transgenic plants expressing cellulase enzymes have taught elimination of the secretion signals to contain the cellulase enzymes in the cytosol of cells. This is not necessary with the use of intein modified proteins and is a substantial improvement as the modified protein may be placed in close proximity with its substrate, but not catalyze the reaction until desired. In addition, these plants have a higher degree of environmental safety. Because the genes transferred encode proteins of substantially less activity under physiological conditions, horizontal gene transfer between species is less likely to impart any selective advantage. For this reason it is unlikely that either the transgenic plants would outperform native plants in the wild, or that gene transfer would yield a selective advantage favoring a transformed population.

Example 2 demonstrates the broad applications of this invention. Example 2 shows a variation of the method of Example 1 to generate a transgenic Douglas-fir species expressing an intein modified lignin peroxidase. The choice of a specific target protein depends upon the application intended for the transgenic plant species. For this example, a lignin peroxidase gene that facilitates the catalytic breakdown of lignin, a chemical component of wood was selected. By using an intein modified lignin peroxidase, the whole plant may be regenerated while the inactivated intein modified lignin peroxidase is produced throughout the plant, at high titer if desirable. The enzyme may be subsequently activated by the self-splicing ability of the intein to yield the native lignin peroxidase at increased activity than the intein modified lignin peroxidase. This allows improved control of the lignin peroxidase activity that is not currently available. Such a transgenic plant species is valuable for the production of pulp, animal feeds, substrates for other processes, improvements on mechanical pulping, biobleaching of pulp, improvement from decreased pulp processing wastes, and the production of biopolymers with unique properties.

Construction of Gene & Intein Modified Protein

As indicated above, any native protein is suitable as the target protein, and its selection is dependent upon the plant's intended purpose. For this example, a Douglas-fir species that may modify its own lignin is beneficial as a substrate for different pulping processes. The protein encoding nucleic acid of interest may be isolated from *Phanerochaete chrysosporium* (GenBank Accession #M37701) [SEQ ID NO: 25]. One primer preferably matches the 5' end of the sense strain to be amplified, and the other the 5' end of the complementing DNA strand at the end of the gene. It is beneficial to have relative sequence uniqueness.

Purification of PCR Fragments from Gel

The purification of the nucleic acid from the gel is accomplished using electroelution, phenol extraction, agarase digestion, glass bead extraction, or from a number of commercially available kits. Preferably the commercially available QIAquick Gel Extraction Kit, available from Qiagen (Valencia, Calif.) is used.

Intein Selection

The choice of intein is very dependent upon both the intended purpose of the plant and the intein modified protein. Many different inteins exist and may be used. For this example an intein with the same properties as in Example 1 is beneficial for the intended use of a transgenic Douglas-fir species. Hence, a variant of the Psp pol intein (GenBank Accession #PSU00707)[SEQ ID NO: 26] from *Pyrrococcus* spp. is preferably used. The advantage of this intein is that upon splicing it yields predominantly ligated, native protein (>75%), and is temperature sensitive so that intein splicing is inhibited at temperatures less than 30° C., and is not substantial until 50° C., where the half-life of the uncleaved protein is less than 2 hours. This intein induces splicing in vitro by a pH shift, thus adding increased flexibility to subsequent processing of the transgenic plant.

Vector Transformation

With the vector contained within the recombinant strain of *A. tumefaciens*, gene transfer to Douglas-fir relies on the bacteria's specialized delivery system. Other gene transfer methods are available, and selection of a suitable transformation method depends upon the source of the plant material and ease with which the method can be applied. Some modification and optimization of the transformation parameters is usually necessary.

Uses of the Recombinant Trees

The tree of Example 2 may be used as a source material for the purification of lignin peroxidase or intein-modified lignin peroxidase. Alternatively, it may be used also by itself as a substrate for producing wood pulp in any number of applications, e.g. paper production, animal feed, composite materials, etc. Both Example 1 and Example 2 have illustrated the use of trees, certainly other plants are useful options and depend upon the intended use of the invention. In many areas these types of trees do not grow well and grasses, vines, seaweed, or other plant species do, and may be used equally well. In addition, many fruits and vegetables may benefit from intein modified protein technology, such as for example to induce ripening, pesticide resistance, or any number of other applications. Hence the choice of host plant is not limiting. The use of plants as sources for recombinant proteins is facilitated by use of the CIVPS or intein technology of this invention. Plants are made to express any number of fusion proteins where the fusion point is comprised of an intein that does not facilitate recombination of fused protein exteins, but instead links the desired protein to a binding protein for purification via affinity chromatography. In this case the desired protein may or may not have full activity in vivo. Once expressed in the plant, the fusion protein is eluted onto an affinity column where the binding portion of the fusion protein binds the column. The column is then treated to induce intein splicing and the desired protein is washed away and recovered. Another variation of the invention that is of medical interest is a fusion protein comprising a therapeutic protein or vaccine fused by inteins to protect protein groups or relying on inteins to disrupt their natural activities when in the plant. Such a therapeutic protein can be expressed in a plant and purified and injected, or simply eaten by a human and non-human animal, e. g. in the case of animal vaccination or hormonal treatment. Intein splicing then occurs either in vitro in a process tank or inside the patient, or animal, relying on the change of pH within the stomach, or a thiol gradient induced by ingestion of a third chemical. Splicing removes the protective protein groups, yielding the native therapeutic protein or vaccine, which is then absorbed in the gut.

Either of the transgenic trees expressing intein modified proteins from Examples 1 and 2 may be effectively used in an industrial scale process as is shown in Example 3. The pulping itself may be enhanced by a modification similar to that used in Example 2 for the Douglas-fir species.

Tree Processing

Typical pretreatment processes for the degradation of lignocellulosic substrates include concentrated acid pretreatment (usually Sulfuric Acid), dilute acid pretreatment, ammonia explosion pretreatment, and hot water pretreatment. Other pretreatment processes are possible, and design of the transgenic tree expressing an intein modified protein should be optimized to take full advantage of a pretreatment process when necessary. Intein splicing may occur in a vessel via any known method, such as, but not limited to: pH shift, temperature change, light exposure, acoustic stimulation, or any exogeneous chemical addition.

Intended Uses and Process Variations

Preferred variations of the process of Example 3 include combining the pretreatment, splicing, digestion, and fermentation steps. This preferred processing consolidation may occur between any of the steps, however a preferred manifestation incorporates all steps simultaneously in a single unit operation. This preferred combination may realize cost savings through a decrease in capital expenditure and depreciation, decrease in the cost of substrates, and a process dependent decrease in the cost of energy and chemicals input to the process. In addition, as opposed to competing chemical processes making the same products, environmental benefits may be realized through decreased emissions and hazardous waste generation. In Example 3 the choice of product is dependent upon the organism used in the fermentation for the desired bioconversion. Any organism that may adequately utilize the degraded cellulose as a substrate may be used to effectively produce a desired product. For this reason the spectrum of end products that may be made is very large. Applications that will benefit from substrates with preferred processing traits facilitated by the intein modified proteins carrying plant of this invention include, but are not limited to, fuel production, chemicals production, textiles production, biopolymer production, food production, and saccharification. Although Example 3 is mostly focused on the fermentation of the degraded transgenic plants, intein modified plants may also be used as substrates for traditional chemical processes. For example, the plants of Example 2 may be preferentially used in paper pulping. In such a process, benefits are derived from a decrease in the harsh chemicals used to bleach the wood. This will likely result in a decrease in the costs of chemical input, hazardous material generation and containment, and potentially some consolidation in processing. Another use is that of pectinase for cotton scouring, or cellulases for other textile production processes. In these instances, the end products are derived from more traditional chemical processes, although benefits accrue through the use of intein modified protein plant substrates, as opposed to the normally harsh chemical processing environment generally employed.

Animal feed is commonly supplemented with a variety of enzymes used to increase the nutritional value of the feed, as well as decrease the environmental burden experienced in proximities where animal manure accumulation is substantial. Nutritional value is increased through the putative enzyme action on plant polymers, which assist the animal in digesting the feed and thereby utilizing more of the beneficial feed components. The environmental burden may be decreased by limiting the amounts of added minerals, such as inorganic phosphate, which may be obtained from the plants themselves in the presence of the active enzyme. The benefits associated with using intein modified proteins, as opposed to unmodified proteins, result in multi-protein expression, at high levels, which do not interfere with plant regeneration yet impart a desired enzyme activity upon splicing within the animals stomach. This decreases the cost of feed by delivering the enzymes within the meal itself, as opposed to their being produced exogenously and added to the meal. In addition, the added benefit of using genes that code for nearly inactive proteins in vivo in plants, provides a technology platform that is less likely to be associated with environmental risks associated with horizontal gene transfer to native plant species. This advantageous environmental affect, whether real or perceived, holds for all intein modified protein plant products. Example 4 illustrates the construction an intein modified phytase in rapeseed, for use as animal feed.

Uses and Variations

Phytase is an enzyme that assists in the evolution of inorganic phosphorous from myoinositol phosphates contained inherently in animal food. An economic impact is brought about through a decrease in the amount of phosphate supplementation required for the production of animal feed, and a decrease in the phosphate content of the animal's manure, which contributes to the contamination of local waters. Although Example 4 below illustrates the construction and use of an intein modified phytase expressed in rapeseed for animal feed, a number of other valuable native proteins may be used as well. For example, phytase may be substituted with, or used in addition to any number of cellulases, amylases, glucanases, hemi-cellulases, pectinases, proteases, xylanases, lipases, growth hormones, or immunogenic antigens, among others. Each of these other proteins has a potential economic value in the use of animal feed supplementation.

Example 5 illustrates one of the preferred embodiments of the invention. A transgenic corn is constructed and used as a substrate for ethanol processing. In this case the intein modified gene sequence of Example 1 is again used for demonstration purposes only. In a preferred embodiment, however, several intein modified proteins may be expressed simultaneously to optimize the desired plant degradation processing trait for use in the fermentation process. The target enzymes may be selected from enzymes commonly known as cellulases (E.C. 3.2.1.4), exocellobiohydrolases (E.C. 3.2.1.91), glucosidases (E.C. 3.2.1.21), and may be expressed optimally with other enzymes selected from the Enzyme Classification heading 3.2.1.x, or any other classification group necessary. In addition to the simultaneous expression of multiple intein modified proteins, the preferred composition of matter embodiment is a fertile plant capable of reproduction and stable gene inheritance.

Transformation Information

The macroprojectiles are used to accelerate the microprojectiles, which enter the plant cells.

Having now generally described this invention, the same will be better understood by reference to certain specific examples, which are included herein for purposes of illustration only, and are not intended to be limiting of the invention or any embodiment thereof, unless and where it is so specified.

EXAMPLES

Example 1

Production of Transgenic Poplar Expressing an Intein-Modified Cellulase

For this example a cellulase enzyme is used. A vector is first assembled containing the DNA coding sequence for the intein modified protein. In order to construct such a vector, an intein modified protein DNA sequence is first prepared, and then packaged into the desired vector. The desired protein for this plant is a cellulase (GenBank Accession #AY039744) [SEQ ID NO: 27] isolated from *Bacillus* sp. NBL420. The gene corresponding to this protein is amplified using PCR from a genomic DNA template isolated from the *Bacillus* sp. NBL420. The PCR reaction is performed by mixing the template DNA, two primers complimentary to the 3' ends of the template DNA to be amplified, Taq DNA polyermase, reaction buffer (10× buffer includes 500 mM KCl, 100 mM Tris-Cl pH 9.0, 0.1% Triton X-100), and $MgCl_2$ in a thin-walled 250 μL PCR tube. Once mixed, each reaction tube is placed in a thermocycler, and the thermocycler is set for 35 cycles comprised of three segments: 94° C. for 30 seconds, 60° C. for 60 seconds, 72° C. for 120 seconds. Following amplification, the resulting PCR product is analyzed by electrophoresis on a 1% agarose gel, along with molecular weight standards (Invitrogen, Carlsbad, Calif.), with the aid of 1×TAE (or TBE) running buffer, and stained with ethidium bromide (0.5 μg/mL). Care should be taken to ensure that the appropriately sized band, of approximately 3200 base pairs (bp), has been obtained. This band is then cut out from the gel with a scalpel, and purified (separated from the gel material) using a commerically available gel purification kit (Qiagen). Once the fragment has been purified from the gel, the band is analyzed using restriction digestion or sequencing as described by Ausubel et. al., Current Protocols in Molecular Biology, Wiley, New York (1998). After gene amplification, the gene is modified by insertion of the intein sequence segment. In this case, a variant of the Psp pol intein (GenBank Accession # PSU00707) [SEQ ID NO: 26] from *Pyrrococcus* spp. is used. This variant, described in the literature, contains a mutation at the tyrosine 534 residue which converts that tyrosine to methionine. See, Xu, M, Perler, F, (1996), The mechanism of protein splicing and its modulation by mutation, The EMBO Journal 15:5146-5153. This intein may be cleaved in vitro by a pH shift. The coding sequence of this intein is then amplified by PCR using genomic DNA from *Pyrrococcus* spp, as a template. The PCR reaction is conducted using a standard protocol (e.g., 30 cycles comprised of a 94° C. for 30 seconds, 50° C. for 60 seconds, 72° C. for 120 seconds) and the following primers.

```
5'-ATTATGTGCATAGAGGAATCCAAAG-3'   [SEQ ID NO: 5]

5'-AGCATTTTACCGGAAGAATGGGTTC-3'   [SEQ ID NO: 6]
```

Once the amplification is complete, the PCR product is transferred to and elecrophoresed on a 1% agarose gel in 1×TAE or TBE buffer. The resulting band is then purified and analyzed as described above for the native cellulase coding sequence. At this point the two PCR fragments shown in FIG. 1, one encoding the cellulase protein and one encoding the intein polypeptide sequence, are joined. Here, the intein is inserted in frame into the native protein, such that a serine residue of the native protein becomes the terminal C-extein amino acid at the junction point between the native intein and C-extein of the native protein. This intein modified protein segment is produced using PCR by first amplifying the C-extein coding sequence of the cellulase gene. Primers that overlap both the C-extein, and the intein end containing the histidine and asparagine codons immediately adjacent to the C-extein are used to amplify the C-extein sequence:

```
5'-CTTTGGATTCCTCTATGCACATAATTCCGGAAACGGCGGTGTCTACCTCG-3'   [SEQ ID NO: 7]

5'-CGTGTCTGCTCCGTTTACCGCTTTTTTTAATTGGACGAATTTGTGCGTGA-3'   [SEQ ID NO: 2]
```

The resulting sequence is 579 nucleotides long. The intein is then amplified using a sense primer that contains both the intein end containing the terminal serine codon, and the N-extein end of the cellulase gene, along with an antisense primer that contains specific nucleotides of the intein and C-extein. For this PCR reaction the following primers are used to obtain a sequence 1661 nucleotides long:

```
5'-ACAGAATGGGGAACGAGCGATGCTAGCATTTTACCGGAAGAATGGGTTC-3'   [SEQ ID NO: 1]

5'-CGAGGTAGACACCGCCGTTTCCGGAATTATGTGCATAGAGGAATCCAAAG-3'  [SEQ ID NO: 8]
```

The N-extein is then amplified using PCR and one primer that contains specific nucleotides of the sense N-extein strand, and another primer that contains specific nucleotides of the N-extein and adjacent intein sequence. The N-extein portion of the cellulase gene is amplified with the following primers resulting in a sequence 988 nucleotides long.

```
5'-AGCATTCAGACCTCCCATTTCATACGAAAAGAGGAAATAGATAGATTTTC-3'  [SEQ ID NO: 9]

5'-GAACCCATTCTTCCGGTAAAATGCTAGCATCGCTCGTTCCCCATTCTGTG-3'  [SEQ ID NO: 10]
```

Once these three reactions are complete, each PCR fragment is cleaned to remove residual primers, and the C-extein, intein, and N-extein PCR fragments are joined by conducting two more polymerase chain reactions. The intein and one of the cellulase extein regions, either the C-extein or the N-extein, are amplified in a single reaction by mixing equimolar portions of the two PCR fragments generated above and performing PCR as described earlier. This reaction requires no extra external primers and results in the first intein-extein fusion. This reaction mixture is cleaned, and then equimolar portions of the cleaned fusion product are mixed with the remaining extein portion, and PCR is conducted once again without adding additional primers. No exogeneous primer is required in either of the last two PCR reactions, and annealing occurs at the intein-extein junctions. The annealed regions are extended by Taq polymerase resulting in the final fusion products. This sequence of reactions results in the coding sequence of the intein modified protein with the intein inserted at the exact position desired. The product of the final reaction is cleaned again, and amplified using PCR one last time with primers specific to the cellulase extein termini with specific ends to facilitate ligation into the cloning vector. Once this reaction is complete, the PCR products are run on an agarose gel, and the appropriate band, 3806 nucleotides long, is purified from the gel and analyzed according to the methods described above. The resulting intein modified protein coding sequence (nucleic acid segment) contains a ribosome binding site, a start codon at the beginning of the N-extein, the complete sequence of the intein modified cellulase with the intein inserted in frame in the proper orientation, and a stop codon at the end of the C-extein coding sequence. The intein modified cellulase coding sequence is then cloned into pTiBo542, replacing the tms and tmr genes in the T DNA, using the methods described in Ausubel, et. al., Current Protocols in Molecular Biology (1998). See, Parsons T J, Sinkar, V P, Stettler, R F, Nester, E W, Gordon, M P, "Transformation of Poplar by *Agrobacterium tumefaciens*," Biotechnology 4:533-536, 1986. Here the expression cassette includes a "MAC" promoter, a mannopine synthetase terminator, and a kanamycin resistance marker. This vector is transformed into *A. tumefaciens* A281 using any suitable method known in the art (e.g., electroploration, or the calcium chloride method).

Various transformation methods are also described by Ausubel, et. al. (1998), above.

To transform the desired Populas trichocarpa×deltoides, H11 plant species, with the recombinant *A. tumefaciens*, a variation of the leaf disk method is employed. The recombinant *A. tumefaciens* is cultured in selective medium containing 50% MG medium (10g/L mannitol, 2.32 g/L sodium glutamate, 0.5 g/L $KH_2PO_4$, 0.2 g/L NaCl, 0.2 g/L $MgSO_4$-$7H_2O$, 0.002 g/L biotin, pH 7.0), 50% luria broth (20g/L tryptone, 10g/L yeast extract, and 10g/L NaCl), and appropriate antibiotic, at 30 0C in an incubator-shaker. For plant transformation, small greenwood stem sections, approximately 7 mm in length and 2-3 mm in diameter, are sterilized with a 20% bleach, 0.1% Tween 20, and 30 mg/L Benomyl systemic fungicide (Chas. H. Lilly Co., Portland, Oreg.) solution. After washing with sterile water, the stem sections are aseptically transferred to a culture of *A. tumefaciens* at a cell concentration of approximately $5\times10^8$ cells per mL, and the sections allowed to incubate for 16 hours. After exposure to the recombinant *A. tumefaciens* culture, the plant stems are transferred to solid Murashige-Skoog medium supplemented with zeatin riboside and kanamycin in a vertical position. See, Murashige T, Skoog F, "A revised medium for rapid growth and bioassays with tobacco tissue cultures," Physiol. Plant, 15:473-497, 1962. Once roots have begun to grow, shoots will develop. The regenerating plants are transferred to fresh plates every two to three weeks, and a normal light cycle is maintained during plant growth and at elevated humidity in the incubator. Once roots form, the explants are transferred to a solid medium lacking zeatin riboside, but containing kanamycin for another two to three weeks, after which period the plants are transferred to boxes containing soil for four to five days prior to replanting in soil and full growth in a greenhouse or controlled plot of soil. Initial plants are screened by several methods to ensure the intein modified cellulase DNA sequence has been transferred to the genome and protein expression is active. Genetic screening is conducted by Southern analysis on genomic DNA isolated from the transgenic plant using the intein modified cellulase coding sequence as a probe, as described by Ausubel, et. al. (1998), above. PCR is conducted using probes specific to the intein modified cellulase coding sequence and the transgenic plant's genomic DNA as a template, as described above. Appearance of the appropriately sized band on an ethidium bromide stained gel verifies the presence of the intein modified cellulase coding sequence. Direct sequencing of the plant's genomic DNA may also be performed. Protein production is monitored by western analysis using antibodies specific to both the intein modified cellulase and the native cellulase. In addition, enzymatic assays for cellulase activity are known in the art and may be used to quantify the activity of the unspilced intein modified cellulase and the spliced cellulase.

Example 2

Production of Transgenic Douglase Fir

Expressing Intein-Modified Lignin Peroxidase

This example uses the same method for constructing the vector containing the intein modified lignin peroxidase coding sequence as used in example one. The primary differences are in the *A. tumefaciens* plasmid employed, the native protein sequence that is modified, and the primers selected to amplify the new intein modified lignin peroxidase coding sequence.

The lignin peroxidase gene (GenBank Accession # M37701) [SEQ ID NO: 25] is amplified by PCR using genomic DNA from *P. chrysosporium* as a template. The primers

```
5'-ATGGCCTTCAAGCAGCTCGTCGCAG-3'   [SEQ ID NO: 11]

5'-TTAAGCACCCGGCGGCGGGGGGCTG-3'   [SEQ ID NO: 12]
```

are used in the PCR reaction as described in example one.

Following amplification, the resulting PCR product is analyzed using gel electrophoresis on an agarose gel, along with molecular weight standards as described in example one. After staining the gel with ethidium bromide, the 1567 base pair (bp) band is cut from the gel with a scalpel, and purified from the gel as described above. After purifying the fragment from the gel, the fragment is analyzed using restriction digestion or sequencing for direct verification as described by Ausubel, et al., 1998.

After the gene is amplified, it is modified by insertion of the intein sequence into the gene sequence. For this example, the same intein is used as in example one. The coding sequence of this intein is amplified in the same manner as described in example one. The resulting intein DNA sequence is purified by gel electrophoresis and analyzed as described previously.

The two PCR fragments, one encoding the lignin peroxidase and one encoding the intein polypeptide sequence, are joined. To ensure proper intein splicing, the intein is inserted in frame next to a serine residue of the lignin peroxidase such that this serine is on the carboxylic acid side, of this intein's histidine-asparagine conserved residues at the terminal 536 and 537 intein amino acid positions, respectively. The intein is inserted into the native protein, such that the serine residue of the native protein becomes the terminal C-extein amino acid at the junction point between the native intein and C-extein of the native protein. The intein is positioned within the native protein such that its presence substantially reduces the activity of the resulting intein modified protein. In most circumstances virtually any serine residue within or near the active site of the molecule will meet this criterion, however some optimization may be necessary.

The intein modified protein sequence is produced using PCR the same as described in example one, with the only difference being the choice of primers. The C-extein portion of the lignin peroxidase gene is amplified using the cleaned gene product from the PCR reaction above, and the following primers resulting in a 445 nucleotide sequence:

```
5'-CTTTGGATTCCTCTATGCACATAATTCTCGCCCGCGACTCCCGCACCGCT-3'   [SEQ ID NO: 13]

5'-TAAGCACCCGGCGGCGGGGGGCTGGAAGAGGAATATGTCAGCTGGGGGC-3'   [SEQ ID NO: 14]
```

The N-extein portion of the lignin peroxidase gene is amplified using the same template, by PCR using the following primers.

```
5'-ATGGCCTTCAAGCAGCTCGTCGCAGCGATTTCCCTCGCACTCTCGCTCAC-3'   [SEQ ID NO: 15]

5'-GAACCCATTCTTCCGGTAAAATGCTGTGTGGTCGGTCTGGATGCGGATCT-3'   [SEQ ID NO: 16]
```

The resulting sequence is 1171 nucleotides long. The intein coding sequence to be placed into the lignin peroxidase gene is amplified using PCR as described in example one. In this reaction use a *Pyrrococcus* spp genomic DNA template and the following primers:

```
5'-AGATCCGCATCCAGACCGACCACACAGCATTTTACCGGAAGAATGGGTTC-3'   [SEQ ID NO: 17]

5'-GCGGTGCGGGAGTCGCGGGCGAGAATTATGTGCATAGAGGAATCCAAAG-3'   [SEQ ID NO: 18]
```

The resulting sequence is 1660 nucleotides long. Once these reactions are complete, the reaction products are electrophoresed on an agarose gel, purified from the gel, and analyzed as described above. The extein and intein portions are joined as described in example one. In this case the intein fragment is mixed with an equamolar portion of the C-extein lignin peroxidase fragment. Combination of these fragments represents both the template and primers required for the PCR reaction. PCR is performed using the same reaction conditions as in example one. Once complete, the PCR products are electrophoresed on a 1% agarose gel, and the appropriate band, 2106 nucleotides long, is purified from the gel. The purified band is analyzed as described in example one. A small amount of the purified reaction product is then quantified by measuring the absorbance at 260 nm and 280 nm on a UV spectrophotometer.

The intein modified protein DNA coding sequence is completed with one more PCR reaction. Equamolar amounts of the fused C-extein and intein fragment just constructed are combined with the N-extein fragment purified previously. The PCR reaction is conducted using the same conditions in the previous reactions. The reaction products are electrophoresed on a 1% agarose gel, the appropriate band, 3302 nucleotides long, is purified from the gel, and analyzed according to the methods described in example one. The final intein modified protein coding sequence has the complete intein sequence in frame, in the proper orientation, within the lignin peroxidase coding sequence.

The intein modified lignin peroxidase coding sequence is cloned into a plant expression cassette. In this case, the pTiA6 plasmid is used with kanamycin resistance and lacking the octupine synthetase genes, but containing the octupine transcription control sequences. The intein modified lignin peroxidase is ligated into a restricted pTiA6 under the octupine transcription control sequences (promoter and 3' polyadenylation site). *A. tumefaciens* K12X562 is transformed using the resulting ligated vector, and any suitable method known in the art (e.g., electroploration, or the calcium chloride method). Transformation methods are described by Ausubel, et. al. (1998).

Douglas-fir is transformed, with the recombinant *A. tumefaciens*, and nodal segments or seeds sampled from these trees. The shoot multiplication and elongation is conducted as previously described (Gupta P K, Durzan, D J, "Shoot multiplication from mature trees of Douglas-fir, and sugar pine," Plant Cell Reports, 9:177-179, 1985) in culture on DCR basal medium plates. A culture of the recombinant *A. tumefaciens* is grown according to the method described in example one. For plant transformation, the regenerated shoots from culture, approximately 50 mm in length, or seeds are surface sterilized by treatment with a 10% bleach and 0.1% Tween 20. Once sterilized, the shoots or seeds are aseptically rinsed with sterile, distilled, and deionized water. The seeds or the shoots are transformed by first wounding the epidermal tissue with a sterile needle or by cutting the surface with a sterile scalpel. The wounded shoots or seeds are soaked in a culture of the recombinant *A. tumefaciens* at a cell concentration of approximately $5\times10^8$ cells per mL. After a 12 hour exposure to the recombinant *A. tumefaciens* culture, the shoots and seeds are cultured in DCR basal medium with 2.2% sucrose and 0.8% Bacto (Difco) agar. The culture conditions include a 16 hour light cycle at 25° C., followed by and 8 hour dark cycle at 20° C. in a green house or growth chamber. The regenerating plants are transferred to fresh plates every two to three weeks. Once roots form, the explants are transferred to boxes containing soil for four to five days prior to replanting in soil and full growth in a greenhouse or controlled plot of soil. The first year of growth is conducted within a green house under controlled temperature conditions, not exceeding 30° C.

The plants are screened using methods similar to those of example one, except specific to the lignin peroxidase protein or intein modified lignin peroxidase protein in the case of western analysis.

The resulting transgenic Douglas-fir species is grown indefinitely while producing the intein modified lignin peroxidase in high titer. The lignin peroxidase is subsequently activated using the same methods described in example one because the same intein was employed for modification in this example.

Example 3

Fermentation Substrate Preparation Process

Using Plants Expressing Intein Modified Protein

In the case of example one, the transgenic poplar species can be used as substrate for ethanol production via fermentation. For this process the transgenic tree is harvested using a suitable tool, such as a chain saw or ax. The tree is subsequently pulped using a mechanical pulper. The pulp is then placed it in a tank. After any necessary pretreatment has been conducted, intein splicing is induced by raising the temperature of the tank and reducing the pH to a value of 4. Depending on the pretreatment used, intein splicing may be stimulated by the pretreatment and thereby occur in parallel with that process operation. Once spliced the native enzyme activity begins digesting the cellulose of the pulp, increasing the concentration of monosaccharides.

Following the induction of splicing, the contents of the saccharification vessel are mixed in any proportion with native poplar pulp or other substrates, to facilitate cellulose degradation of those substrates. The proportion of the mixing depends upon the cellulase activity of the transgenic poplar which is a function of the amount of intein modified cellulase expressed in the plant, the efficiency of splicing, the efficiency of recombination, and the activity of the recombined, native cellulase on the substrate. Each one of those parameters has a broad spectrum of possible values and can be optimized to facilitate process economics.

The resulting glucose is then filter sterilized from the degraded cellulose through a 0.22 (or less) μm filter, or heat sterilized in batch or continuous mode through a heat exchanger. The sterilized glucose is fed to a fermentation process, where it can be used as a substrate for ethanol production as described in the literature. See, H. K. Sreenath and T. W. Jeffries, "Production of ethanol from wood hydrolysate by yeasts," Bioresource Technology, 72(3): 253-260, 2000; Lisbeth Olsson and Barbel Hahn-Hagerdal, "Fermentation of lignocellulosic hydrolysates for ethanol production," Enzyme and Microbial Technology, 18(5):312-331, 1996; Kutluo O. Ulgen, et. al., "Bioconversion of starch into ethanol by a recombinant *Saccharomyces cerevisiae* strain YPG-AB", Process Biochemistry, 37(10):1157-1168, 2002; M. Mete Altintas, et al, "Improvement of ethanol production from starch by recombinant yeast through manipulation of environmental factors," Enzyme and Microbial Technology, 31(5):640-647, 2002; Farooq Latif, et al., "Production of ethanol and xylitol from corn cobs by yeasts," Bioresource Technology, 77(1):57-63, 2001.

The fermentation process is conducted in batch, fed-batch, or continuous modes.

Example 4

Plants Expressing an Intein Modified Protein used for Animal Feed

A transgenic rapeseed is constructed following essentially the same methods described in Examples 1 and 2 above, with the following modifications. In constructing the CIVPS or intein modified gene sequence, the same intein coding sequence can be used, however in this case it is fused within the phytase expressed by *Aspergillus ficuum*. In this example the selected intein modified protein relies upon the acidity of the animal's stomach to induce protein splicing. The selected phytase was chosen because of its high level of activity at low pH (van Ooijen et al. (2000), United States Patent Publication No. 6,022,846). The C-extein portion of the phytase is amplified using the following primers under the same conditions as previously described.

```
5'-CTTTGGATTCCTCTATGCACATAATTTCCTTCGACACCATCTCCACCAGCA-3' [SEQ ID NO: 19]

5'-CTAAGCAAAACACTCCGCCCAATCACCGCCAGATCTGGCAAAGCTCAACC-3'  [SEQ ID NO: 20]
```

The resulting sequence is 627 nucleotides long. The intein sequence is amplified using primers under the same conditions as previously described.

```
5'-AGTGACCTACCTCATGGACATGTGCAGCATTTTACCGGAAGAATGGGTTC-3'  [SEQ ID NO: 21]

5'-GCTGGTGGAGATGGTGTCGAAGGAATTATGTGCATAGAGGAATCCAAAG-3'   [SEQ ID NO: 22]
```

Finally the N-extein is amplified using primers resulting in a PCR fragment 928 nucleotides long.

```
5'-ATGGGTGTCTCTGCCGTTCTACTTCCTTTGTACCTCCTGTCCGGAGTATG-3'  [SEQ ID NO: 23]

5'-GAACCCATTCTTCCGGTAAAATGCTGCACATGTCCATGAGGTAGGTCACT-3'  [SEQ ID NO: 24]
```

The resulting DNA fragments are cleaned and analyzed, then combined using PCR and the associated methods described in Examples 1 and 2. This procedure results in the intein modified phytase coding sequence. The final composite intein modified phytase sequence is then amplified, cleaned and analyzed as described in Examples 1 and 2. The intein modified phytase DNA coding sequence is cloned into the same expression cassette, and used to transform *A. tumefaciens* as described in Example 2. Rapeseed stem segments are transformed using the resulting recombinant *A. tumefaciens*. Transformation occurs substantially as described in Examples 1 and 2 with the following modifications. The rapeseed stem segments are surface sterilized from five to six week-old plants using a 20% bleach solution for 25 minutes at room temperature. Following sterilization, the stem segments are aseptically rinsed with sterile, distilled, and deionized water. The segments are preconditioned by incubation for 24 hours on Murashige-Skoog medium supplemented with 1 mg/L of BAP. Once the 24 hours has transpired, the stem segments are incubated for 48 hours with the newly transformed strain of *A. tumefaciens* containing the intein modified phytase. Following this incubation step, regenerate transgenic plants and select them using the kanamycin resistance marker, following substantially the same procedures described in Examples 1 and 2. Confirmation of incorporation of the intein modified phytase can also be conducted as described in Examples 1 and 2.

The resulting transgenic rapeseed is grown in an approved area according to local legislation. The rapeseed is harvested when it's mature and used to supplement animal feed. Conversely, the rapeseed can be grown on grazing land for the animals since intein splicing should occur spontaneously in the animal's stomach, allowing for activation of the phytase activity.

Example 5

Production of Transgenic Maize Expressing an Intein Modified

Cellulase and Utilization in the Production of Ethanol

This example illustrates one way in which the invention may be practiced. Here, transgenic corn is constructed and used as a substrate for ethanol processing, or as a substrate in other fermentations. In this example the intein modified gene sequence of Example 1 is again used for demonstration. The growth of *Zea mays* friable, embryogenic type II callus cultures is initiated from immature embryos, approximately 1.6 mm to 1.8 mm in length, from greenhouse grown A188 (University of Minnesota, Crop Improvement Association)×B73 (Iowa State University) plants. After harvest, fragments are surface sterilized using 50% bleach, for 25 minutes at room temperature, and then washed with sterile, distilled, deionized water. New cultures are aseptically initiated from the harvested fragments and maintained under no more than 10 $\mu E\ m^{-2}\ s^{-1}$ light, at 24° C., on modified N6 medium (Chu, et al., (1975), "Establishment of an Efficient Medium for Anther Culture of Rice through Comparative Experiments on Nitrogen Sources," Sci. Sin., 18:659-668) at pH 5.8, with 2 mg/L glycine, 2.9 g/L L-proline, 1 mg/L 2,4-dichlorophenoxyacetic acid (2,4-D), 100 mg/L casein hydrolysate, 20 g/L sucrose, and solidified with 2 g/L Gelgro (ICN Biochemicals).

After approximately two weeks of incubation, the cultures are manually evaluated for proper morphology. This entails visual observation for friable consistency in the presence of well-characterized somatic embryos. Proliferations demonstrating proper morphology are transferred to fresh modified N6 medium (described above). Tissues resulting with the proper morphology are routinely subcultured every two to three weeks, until the microprojectile bombardment is prepared. The desired intein modified gene sequence and expression vector can be constructed as described in Example 1. In this example, the preferred expression vector also has the following alterations. Replace the kanamycin resistance marker with a hygromycin resistance marker using methods known in the art (for example, PCR of the hygromycin resistance marker from a suitable template, DNA endonuclease restriction of the vector, followed by purification, and ligation of the hygromycin resistance marker) as described by Ausubel, et. al., 1998. Once constructed, the vector is precipitated in a 1:1 molar ratio onto either tungsten (average diameter 1.2 μm, GTE Sylvania), or gold, particles. As with other steps in this procedure, the precipitation parameters may require some minor optimization. The precipitation is performed by combining 1.25 mg of the tungsten particles, and 25 μg of the vector DNA in solution with 1.1 M $CaCl_2$ and 8.7 mM spermidine at a total volume of 575 μL. The precipitate is vortexed for 10 minutes at 0° C. Once vortexed, the mixture is centrifuged at 500×g for five minutes. After centrifugation, the supernatant, approximately 550 μL, is removed and the remaining 25 μL of precipitate is dispensed in 1 μL aliquots onto macroprojectiles (Biolistics, Inc, Ithaca, N.Y.) for bombardment as described by Klein et al. (1987), except for the changes noted above. All manipulations are performed aseptically and on ice.

Once the biolistic projectiles are ready, the desired plant tissues are prepared for the bombardment procedure. Any number of callus clumps are aseptically arranged, each weighing 50 mg (wet weight), in an x-pattern near the center of a sterile 60×15 mm petri dish (Falcon 1007). Several dishes should be prepared for each bombardment procedure. These dishes are each paced in turn, 5 cm below the stopping plate of the microprojectile instrument. The dishes are centered below the device, with the lids removed, and a 3×3 mm mesh screen covering the top of the plate. The mesh screen helps contain bombarded tissue within the dish during the procedure. The tissue bombardment is performed with the microprojectile instrument as described by the manufacturer's instructions; commercial microprojectile instruments are available through Bio-Rad (Hercules, Calif.). Following bombardment, the callus are transferred to fresh modified N6 medium plates and cultured under the same conditions used above.

The selection of transformed cells for subsequent regeneration is began after two days of culture. The callus plates subjected to the bombardment procedure are aseptically transferred to fresh, sterile, modified N6 medium plates formulated to a final concentration of 10 mg/L hygromycin B (Calbiochem). After two weeks of exposure, all callus are aseptically transferred from the selective plates to fresh, sterile, modified N6 medium plates formulated to a final concentration of 50 mg/L hygromycin B. This transfer is conducted so that only five 30 mg pieces of callus are contained on a single plate, resulting in an expansion of the number of plates used. Following three weeks on the 50 mg/L hygromycin B plates, all callus are aseptically transferred to fresh, sterile, modified N6 medium plates formulated to a final concentration of 60 mg/L hygromycin B. After two weeks of incubation, the callus are inspected for proliferating clumps. Selected proliferating clumps are transferred to a modified Murashige-Skoog medium supplemented with 0.5 mg/L thiamine-HCl, 0.75 mg/L 2,4-D, 50 g/L sucrose, 150 mg/L asparagines, and 2.0 g/L Gelgro.

At this point it is prudent to ensure transformation of the selected plants. The presence of the intein modified cellulase is verified using the methods described in Examples 1 and 2. In this case, either or both of the intein modified cellulase coding sequence, and the hygromycin resistance marker can be used as the subject of the transformation validation, using methods known in the art, as described by Ausubel, et al., 1998. After two weeks on the modified Murashige-Skoog medium, the plates are exposed to a light cycle incubation regimen composed of 14 hours of light, followed by 10 hours of dark, at 24° C. Plantlets that form are aseptically transferred to 1 L, wide mouthed Erlenmeyer flasks containing 100 mL of the modified Murashige-Skoog medium. The resulting plants are transferred to vermiculite for one to two weeks prior to plantation in soil and growth to maturity. The mature plants are analyzed substantially as described in Example 1 to ensure stable transformation of the intein modified protein sequence, and preferentially, expression of the intein modified cellulase.

The resulting mature plants may be cross-pollinated using standard techniques. This can be done either between transformed plants, or between a single transformed plant and an untransformed plant. The progeny resulting from the breeding are screened for containment of the intein modified cellulase, as well as the hygromycin resistance marker. Note, at this point the hygromycin resistance marker used in the selection is no longer an essential element for the use and application of the constructed transgenic corn plants. So long as the intein modified cellulase sequence is contained, retention of the hygromycin resistance marker is not an essential component of the transgenic corn. Seed can be harvested from the fertile transgenic plants and used for plant expansion. The resulting transgenic plants can be grown for use in processes similar to those described in Example 3. The process using a transgenic corn species expressing multiple intein modified proteins, would have the economic advantages of utilizing both the starch and cellulosic portions of the corn plant, consolidating the pretreatment, saccharification, and fermentation steps, and decreased energy and raw material input costs. Effective use of this process for the production of ethanol would be enabled by the inclusion of the intein modified proteins in the transgenic plant.

The enclosed examples do not in any way limit the scope of this patent, as they solely provided to help illustrate applications of the invention disclosed in this patent. Other variations are possible as an artisan would know, and are included within the four corners of this invention.

BIBLIOGRAPHY

Dale, Biotechnol. Prog. 15:775-776 (1999).

Committee on Biobased Industrial Products, Biobased Industrial Products: Priorities for Research and Commercialization, National Academy Press, Washington D.C. (1999).

Cameron, et al., Biotechnol. Prog. 14:116-125 (1998).

Park, et al., Biotechnol. Prog. 14:699-704 (1998).

Taylor, et al., Biotechnol. Prog. 16:541-547 (2000).

Poirier, Nature Biotechnology 17:960-961 (1999).

Lynd, Biotechnol. Prog. 15:777-793 (1999).

Ingram, Biotechnol. Prog. 15:855-866 (1999).

Aspergren, et al., Molecular Breeding 1:91-99 (1995).

Mansfield, et al., Biotechnol. Prog. 15:804-816 (1999).

Evans, et al., Protein Science 7:2256-2264 (1998).

Perler, et al., Nucl. Acids Res. 22:1125-1127 (1994).

Xu, et al., EMBO 15:5146-5153 (1996).

Wood, et al., Biotechnol. Prog. 16:1055-1063 (2000).

Clarke, P.N.A.S. (USA) 91:11084-11088 (1994).

Derbyshire, et al., P.N.A.S. (USA) 95:1356-1357 (1998).

Perler, et al., Nucleic Acids Res. 22:1125-1127 (1994).

Wallace, C. J., Protein Sci. 2:697-705, (1993).

Xu, et al., Cell 75:1371-1377 (1993).

Pietrokovski, S., Protein Sci. 3735:2340-2350 (1994).
Ausubel, et al., "Current Protocols in Molecular Biology," Wiley, N.Y. (1998).
Draper, et al., "Plant Genetic Transformation and Gene Expression: A Laboratory Manual," Blackwell Scientific Publications, Boston (1998).
Potrykus, et al., "Gene Transfer to Plants," Springer, N.Y. (1995).
Guilley, et al., Cell, 30:763 (1982).
Higgins, T. J. V., Annu. Rev. Plant Physiol. 35:191(1984).
Coruzzi, et al., EMBO J. 3:1671 (1984).
Tingey, et al., EMBO J. 6:3565 (1987).
Ryan, et al., Nuc. Acids Res. 17:3584 (1989).
Rocha-Sosa, et al., EMBO J. 8:23 (1989).
Wenzler, et al., Plant Mol. Biol. 12:41 (1989).
Bird et al., Plant Mol. Biol. 11:651 (1988).
Brederode, et al., Nucl. Acids Res. 8:2213 (1980).
Smeekens, et al., T.I.B.S. 15:73 (1990).
van den Broeck et al., Nature 313:358 (1985).
Schreier, et al., EMBO J. 4:25 (1985).
Tague, et al., Plant Phys. 86:506 (1988).
Von Heijne, G., J. Mol. Biol. 189:239 (1986).
Sijmons, et al., Bio/Technol. 8:217 (1990).
Gordon-Kamm, et al., The Plant Cell 2:603 (1990).
Shimamoto, et al., Nature 338:274 (1989).
Horsch, et al., Science 2:1229 (1985).
Ziegler, et al., Molecular Breeding 6:37-46 (2000).
Dai, et al., (a), Molecular Breeding 6:277-285 (2000).
Dai, et al., (b), Molecular Breeding 9:43-54 (2000).
Montvalvo-Rodriguez, et al., Biotech. and Bioeng. 2:151-159 (2000).
U.S. Pat. No. 6,022,846.
Chu, et al., Sci. Sin. 18:659-668 (1975).
Klein, et al., Nature 327:70-73 (1987).

The invention now being fully described, it will be apparent to one of ordinary skill in the art that many changes and modifications can be made thereto without departing from the spirit or scope of the invention as set forth herein.

What is claimed is:

1. A recombinant plant composition of matter in the form of a recombinant plant, plant part, plantlet, tissue, cell, subcellular fraction, seed, seedling, protoplast, progeny or descendent, the recombinant plant composition of matter comprising an expression construct that encodes at least one modified protein comprising a target protein and a *Pyrococcus* spp. polymerase. Psp pol, intein sequence fused within the target protein, wherein the target protein is a lignocellulosic degrading protein and the Psp pol intein sequence is thermally inducible to cause cis splicing of the modified protein by the recombinant plant composition of matter having a temperature of 50° C. or higher.

2. The recombinant plant composition of matter of claim 1, wherein the expression construct comprises, operatively linked to one another, a first nucleic acid segment encoding the modified protein and a second nucleic acid segment including at least one sequence from the group consisting of a selectable marker encoding sequence, a reporter gene and a promoter.

3. The recombinant plant composition of matter of claim 2 including the selectable marker encoding sequence and the promoter, wherein the selectable marker confers resistance to at least one chemical selected from the group consisting of bromoxynil, mannose, 2,2-dichloropropionic acid, G418, haloxyfop, hygromycin, imidazoline, kanamycin, methotrexate, neomycin, phosphinothricin, sethoxydim, 2,2-dichloropropionic acid, glyphosate, hygromycin, trichothecne, sulfonylurea, s-triazine and triazolopyrimidine; and the promoter precedes the first nucleic acid segment.

4. The recombinant plant composition of matter of claim 1, wherein the recombinant plant, plant part, plantlet, cell, seed, seedling, protoplast, progeny, or descendant is fertile and the at least one modified protein is heritable.

5. The recombinant plant composition of matter of claim 1, wherein the recombinant plant, plant part, plantlet, cell, seed, seedling, protoplast, progeny, or descendant is not fertile.

6. An inbred genetically recombinant plant, or plant part, plantlet, tissue, cell, subcellular fraction, seed, seedling, protoplast, progeny or descendent of the recombinant plant composition of matter of claim 1.

7. A genetic hybrid of the recombinant plant, plant part, plantlet, tissue, cell, subcellular fraction, seed, seedling, protoplast, progeny or descendent of the recombinant plant composition of matter of claim 1.

8. The recombinant plant composition of matter of claim 1, wherein the Psp pol intein sequence is inserted immediately before Ser, Thr or Cys of the target protein.

9. The recombinant plant composition of matter of claim 1, wherein the Psp pol intein sequence includes an amino terminus comprising Ser, Thr or Cys.

10. The recombinant plant composition of matter of claim 1, wherein the portion of the expression construct that encodes the target protein is derived from a microorganism.

11. The recombinant plant composition of matter of claim 1, wherein the Psp pol intein sequence includes a carboxy terminus comprising His, Asn, Ser, Thr or Cys.

12. The recombinant plant composition of matter of claim 1, wherein the recombinant plant composition of matter is derived from one of the group consisting of corn, switchgrass, sugar cane, wheat, sorghum, Miscanthus, cotton, alfalfa, and barley.

13. The recombinant plant composition of matter of claim 1, wherein the target protein catalyzes a reaction that includes an activity selected from the group consisting of degrading lignin, degrading cellulose, and degrading hemicellulose.

14. The recombinant plant composition of matter of claim 1 wherein the target protein is a cellulase or a segment thereof.

15. A recombinant plant composition of matter in the form of a recombinant plant, plant part, plantlet, tissue, cell, subcellular fraction, seed, seedling, protoplast, progeny or descendent, the recombinant plant composition of matter comprising a nucleic acid segment encoding at least one modified protein comprising a target protein, which is internally fused with a *Pyrococcus* spp, polymerase, Psp pol, intein sequence;

wherein the target protein is a cell wall degrading enzyme; and wherein the Psp pol intein sequence is thermally inducible to cause cis splicing of the modified protein by the recombinant plant composition of matter having a temperature of 50° C. or higher.

16. The recombinant plant composition of matter of claim 15, wherein the cell wall degrading enzyme is a cellulase.

17. The recombinant plant composition of matter of claim 15 further comprising a second nucleic acid segment encoding a second modified protein comprising a second target protein, which is fused to a second intein sequence;

wherein the second target protein is an enzyme or a segment thereof that catalyzes a reaction producing a monosaccharide.

18. The recombinant plant composition of matter of claim 15 further comprising a second nucleic acid segment encoding a second modified protein comprising a second target protein, which is fused to a second intein sequence;

wherein the second target protein is an enzyme or a segment thereof that catalyzes a reaction producing glucose.

19. The recombinant plant composition of matter of claim 15 further comprising a second nucleic acid segment encoding a second modified protein comprising a second target protein, which is fused to a second intein sequence;

wherein the second target protein is an enzyme or a segment thereof that catalyzes a reaction producing fructose.

20. The recombinant plant composition of matter of claim 15 further comprising a second nucleic acid segment encoding a second modified protein comprising a second target protein, which is fused to a second CIVPS or intein sequence;

wherein the second target protein is an enzyme or a segment thereof that catalyzes oxidation of a sugar.

21. The recombinant plant composition of matter of claim 15 further comprising a second nucleic acid segment encoding a second modified protein comprising a second target protein, which is fused to a second intein sequence;

wherein the second target protein is an enzyme or a segment thereof that catalyzes a reaction producing ethanol.

22. The recombinant plant composition of matter of claim 15 further comprising a second nucleic acid segment encoding a second modified protein comprising a second target protein, which is fused to a second intein sequence;

wherein the second target protein is an enzyme or a segment thereof that includes an activity selected from the group consisting of degrading dextrin, degrading pectin, degrading lipids, degrading protein, degrading chitin, and saccharification.

23. The recombinant plant composition of matter of claim 15 further comprising a second nucleic acid segment encoding a second modified protein comprising a second target protein, which is fused to a second intein sequence;

wherein the second target protein is an enzyme or a segment thereof that catalyzes a reaction including a product selected from the group consisting of phenol, glycerol, ethylene, propylene, toluene, ethyl benzene, styrene, xylene, ethylene glycol, butadiene, formaldehyde, isopropanol, acetone, butanediol, methanol, propanol, butanol, propanediol, a vitamin, methane, ethane, propane, butane, pentane, hexane, heptane, octane, and benzene.

24. The recombinant plant composition of matter of claim 1, wherein the expression vector includes a modified protein coding sequence that is optimized for plant expression.

25. The recombinant plant composition of matter of claim 1, wherein the target protein coding sequence is optimized for plant expression.

26. The recombinant plant composition of matter of claim 1, wherein the Psp pol intein sequence coding sequence is optimized for plant expression.

27. The recombinant plant composition of matter of claim 1, wherein the target protein is a xylanase.

28. The recombinant plant composition of matter of claim 15, wherein the cell wall degrading enzyme is a xylanase.

29. The recombinant plant composition of matter of claim 1, wherein the Psp pol intein sequence is a variant Psp pol intein sequence.

30. The recombinant plant composition of matter of claim 29, wherein the Psp pol intein sequence is encoded by a nucleic acid having the sequence of nucleotides 1839-3449 of SEQ ID NO: 26.

31. The recombinant plant composition of matter of claim 1, wherein the lignocellulosic degrading protein is selected from the group consisting of endocellulases and exocellulases.

32. The recombinant plant composition of matter claim 1, wherein the lignocellulosic degrading protein is an enzyme selected from the group consisting of cellulases having the classification E.C. 3.2.1.4 exocellobiohydrolases having the classification E.C. 3.2.1.91, and glucosidases having the classification E.C. 3.2.1.21.

33. The recombinant plant composition of matter of claim 1, wherein the lignocellulosic degrading protein is a cellulase having the classification E.C. 3.2.1.4.

34. The recombinant plant composition of matter of claim 15, wherein the Psp pol intein sequence is a variant Psp pol intein sequence.

35. The recombinant plant composition of matter of claim 34, wherein the Psp pol intein sequence is encoded by a nucleic acid having the sequence of nucleotides 1839-3449 of SEQ ID NO: 26.

36. The recombinant plant composition of matter of claim 15, wherein the cell wall degrading enzyme is selected from one of the group consisting of cellulase, hemi-cellulase, xylanase, ligninase, and lignin peroxidase.

37. The recombinant plant composition of matter of claim 15, wherein the cell wall degrading enzyme is selected from the group consisting of endocellulases and exocellulases.

38. The recombinant plant composition of matter of claim 15, wherein the cell wall degrading enzyme is an enzyme selected from the group consisting of cellulases having the classification E.C. 3.2.1.4, exocellobiohydrolases having the classification E.C. 3.2.1.91, and glucosidases having the classification E.C. 3.2.1.21.

39. The recombinant plant composition of matter of claim 15, wherein the cell wall degrading enzyme is a cellulase having the classification E.C. 3.2.1.4.

40. The recombinant plant composition of matter of claim 15, wherein the modified protein has an activity identical to a protein encoded by a nucleic acid having the sequence of SEQ ID NO: 28.

41. The recombinant plant composition of matter of claim 15, wherein the modified protein is encoded by a nucleic acid having the sequence of SEQ ID NO: 28.

* * * * *

```
                      SEQUENCE LISTING

<160> NUMBER OF SEQ ID NOS: 28

<210> SEQ ID NO 1
<211> LENGTH: 49
<212> TYPE: DNA
<213> ORGANISM: Artificial Sequence
<220> FEATURE:
<223> OTHER INFORMATION: Primer

<400> SEQUENCE: 1

acagaatggg gaacgagcga tgctagcatt ttaccggaag aatgggttc                 49


<210> SEQ ID NO 2
<211> LENGTH: 50
<212> TYPE: DNA
<213> ORGANISM: Artificial Sequence
<220> FEATURE:
<223> OTHER INFORMATION: Primer

<400> SEQUENCE: 2

cgtgtctgct ccgtttaccg cttttttaa ttggacgaat ttgtgcgtga                 50


<210> SEQ ID NO 3
<211> LENGTH: 50
<212> TYPE: DNA
<213> ORGANISM: Artificial Sequence
<220> FEATURE:
<223> OTHER INFORMATION: Primer

<400> SEQUENCE: 3

agcattcaga cctcccattt catacgaaaa gaggaaatag atagattttc                50


<210> SEQ ID NO 4
<211> LENGTH: 50
<212> TYPE: DNA
<213> ORGANISM: Artificial Sequence
<220> FEATURE:
<223> OTHER INFORMATION: Primer

<400> SEQUENCE: 4

cgtgtctgct ccgtttaccg cttttttaa ttggacgaat ttgtgcgtga                 50


<210> SEQ ID NO 5
```

-continued

```
<211> LENGTH: 25
<212> TYPE: DNA
<213> ORGANISM: Artificial Sequence
<220> FEATURE:
<223> OTHER INFORMATION: Primer

<400> SEQUENCE: 5

attatgtgca tagaggaatc caaag                                    25


<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6

agcattttac cggaagaatg ggttc                                    25


<210> SEQ ID NO 7
<211> LENGTH: 50
<212> TYPE: DNA
<213> ORGANISM: Artificial Sequence
<220> FEATURE:
<223> OTHER INFORMATION: Primer

<400> SEQUENCE: 7

ctttggattc ctctatgcac ataattccgg aaacggcggt gtctacctcg          50


<210> SEQ ID NO 8
<211> LENGTH: 50
<212> TYPE: DNA
<213> ORGANISM: Artificial Sequence
<220> FEATURE:
<223> OTHER INFORMATION: Primer

<400> SEQUENCE: 8

cgaggtagac accgccgttt ccggaattat gtgcatagag gaatccaaag          50


<210> SEQ ID NO 9
<211> LENGTH: 50
<212> TYPE: DNA
<213> ORGANISM: Artificial Sequence
<220> FEATURE:
<223> OTHER INFORMATION: Primer

<400> SEQUENCE: 9

agcattcaga cctcccattt catacgaaaa gaggaaatag atagattttc          50


<210> SEQ ID NO 10
<211> LENGTH: 50
<212> TYPE: DNA
<213> ORGANISM: Artificial Sequence
<220> FEATURE:
<223> OTHER INFORMATION: Primer

<400> SEQUENCE: 10

gaacccattc ttccggtaaa atgctagcat cgctcgttcc ccattctgtg          50


<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
```

-continued

```
atggccttca agcagctcgt cgcag                                        25


<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12

ttaagcaccc ggcggcgggg ggctg                                        25


<210> SEQ ID NO 13
<211> LENGTH: 50
<212> TYPE: DNA
<213> ORGANISM: Artificial Sequence
<220> FEATURE:
<223> OTHER INFORMATION: Primer

<400> SEQUENCE: 13

ctttggattc ctctatgcac ataattctcg cccgcgactc ccgcaccgct             50


<210> SEQ ID NO 14
<211> LENGTH: 49
<212> TYPE: DNA
<213> ORGANISM: Artificial Sequence
<220> FEATURE:
<223> OTHER INFORMATION: Primer

<400> SEQUENCE: 14

taagcacccg gcggcggggg gctggaagag gaatatgtca gctgggggc              49


<210> SEQ ID NO 15
<211> LENGTH: 50
<212> TYPE: DNA
<213> ORGANISM: Artificial Sequence
<220> FEATURE:
<223> OTHER INFORMATION: Primer

<400> SEQUENCE: 15

atggccttca agcagctcgt cgcagcgatt tccctcgcac tctcgctcac             50


<210> SEQ ID NO 16
<211> LENGTH: 50
<212> TYPE: DNA
<213> ORGANISM: Artificial Sequence
<220> FEATURE:
<223> OTHER INFORMATION: Primer

<400> SEQUENCE: 16

gaacccattc ttccggtaaa atgctgtgtg gtcggtctgg atgcggatct             50


<210> SEQ ID NO 17
<211> LENGTH: 50
<212> TYPE: DNA
<213> ORGANISM: Artificial Sequence
<220> FEATURE:
<223> OTHER INFORMATION: Primer

<400> SEQUENCE: 17

agatccgcat ccagaccgac cacacagcat tttaccggaa gaatgggttc             50


<210> SEQ ID NO 18
<211> LENGTH: 49
<212> TYPE: DNA
```

-continued

<213> ORGANISM: Artificial Sequence
<220> FEATURE:
<223> OTHER INFORMATION: Primer

<400> SEQUENCE: 18
gcggtgcggg agtcgcgggc gagaattatg tgcatagagg aatccaaag 49

<210> SEQ ID NO 19
<211> LENGTH: 51
<212> TYPE: DNA
<213> ORGANISM: Artificial Sequence
<220> FEATURE:
<223> OTHER INFORMATION: Primer

<400> SEQUENCE: 19
ctttggattc ctctatgcac ataatttcct tcgacaccat ctccaccagc a 51

<210> SEQ ID NO 20
<211> LENGTH: 50
<212> TYPE: DNA
<213> ORGANISM: Artificial Sequence
<220> FEATURE:
<223> OTHER INFORMATION: Primer

<400> SEQUENCE: 20
ctaagcaaaa cactccgccc aatcaccgcc agatctggca aagctcaacc 50

<210> SEQ ID NO 21
<211> LENGTH: 50
<212> TYPE: DNA
<213> ORGANISM: Artificial Sequence
<220> FEATURE:
<223> OTHER INFORMATION: Primer

<400> SEQUENCE: 21
agtgacctac ctcatggaca tgtgcagcat tttaccggaa gaatgggttc 50

<210> SEQ ID NO 22
<211> LENGTH: 49
<212> TYPE: DNA
<213> ORGANISM: Artificial Sequence
<220> FEATURE:
<223> OTHER INFORMATION: Primer

<400> SEQUENCE: 22
gctggtggag atggtgtcga aggaattatg tgcatagagg aatccaaag 49

<210> SEQ ID NO 23
<211> LENGTH: 50
<212> TYPE: DNA
<213> ORGANISM: Artificial Sequence
<220> FEATURE:
<223> OTHER INFORMATION: Primer

<400> SEQUENCE: 23
atgggtgtct ctgccgttct acttcctttg tacctcctgt ccggagtatg 50

<210> SEQ ID NO 24
<211> LENGTH: 50
<212> TYPE: DNA
<213> ORGANISM: Artificial Sequence
<220> FEATURE:
<223> OTHER INFORMATION: Primer

<400> SEQUENCE: 24
gaacccattc ttccggtaaa atgctgcaca tgtccatgag gtaggtcact 50

<210> SEQ ID NO 25
<211> LENGTH: 5710
<212> TYPE: DNA
<213> ORGANISM: Phanerochaete chrysosporium

<400> SEQUENCE: 25

```
agctcacttt acctatacac atctgcattc agtccttcca gttctctgac cctaacatcc     60
ggtaaatgta ccttcagtga tcgggacgga aggtatgggc ctttcgcata ggtgggtaat    120
ctgcgactgt atgttttgta tggtaccctg agacagtcac ttactgtttc tgctcgctcc    180
aggtaccatt gtcccgcctc tgcgtgattt ccgaggctgg actggcccat ctctgcccac    240
cctgtcctca tctgccaaga gccatcggaa tgccaagccg tgaccactcc aaccggtccc    300
gttctctcag ccactgcgca agtttcttac aggagggctg cttcgccgtt cattcgcggc    360
ctccggatag ctagcgagct tcgatgctcg tggccaatta tggaagcagt cgttgatcgc    420
accggtcccg tactgccttc gctcacaagc cgtgttgttg cgagactctc attcgctggc    480
tcagggtatt gtgcctgttt gctgaggcac agtgcagtca atacacactt gtctcgtcag    540
gacgcggttt gacattccgt ggtgcgtgaa acggtataaa agggatacgc gatttgcagc    600
atatcctcag gccattcgtc ttctacagcc caagttccaa gtcaaacggt catggccttc    660
aagcagctcg tcgcagcgat ttccctcgca ctctcgctca ccactgccaa tggtacgcac    720
cgcttctgca tgctgtgata acgggccccg actaacgcct ccgctgcagc cgccgtggtc    780
aaggagaagc gcgccacctg ctccaacggc gccaccgttg gcgacgcgtc ctgctgtgct    840
tggttcgatg tcctcgacga catacagcag aacctgttcc aaggaggcca gtgcggcgct    900
gaggcccacg agtctatccg tctgtaagtc aatacgctgg tgttgcgcca aggtcataga    960
ttcactttgc tgcagcgtgt tccacgatgc tattgccatc tctcctgcta tggaggccca   1020
gggcaagttc gggtatgtct ttccggcatg gcaatatttt acagcagaca ctgagatatt   1080
gcgcagcggt ggtggtgctg acggctccat catgatcttc gacgacatcg agcccaactt   1140
ccaccctaac attggcctcg acgagattat caacctccag aagccgttcg tccagaagca   1200
cggtgtcacc cctggtgact tcatcgcctt cgccggtgct gtcgcgctca gcaactgccc   1260
gggtgcccca cagatgaact tcttcactgg tcgtcgtcct ggtacgtctc ctctacgaat   1320
cgatctcgac acctcattca tatcgcctta tagctaccca gcccgcaccc gatggtctcg   1380
ttcccgagcc tttccgtgag tttgcagacc acttcatcgc atagttctta gctgacctct   1440
tcatcgcata gttcttagct gacttcagca cagacaccgt cgaccagatc atcgctcgtg   1500
ttaacgatgc cggcgagttc gacgagctcg agcttgtctg gatgctttcc gcgtaagtga   1560
ctgccgcctc gaatttccat cccgacttac accccgattc agccactccg ttgctgcagt   1620
caacgacgtg gacccgaccg tccagggcct gcccttcgac tccacccccg gaatcttcga   1680
ctcgcagttc ttcgtcgaga ctcagttccg tggtatcctc ttccccggct ccggtggcaa   1740
ccagggtgag gtcgagtccg gtatggctgg cgagatccgc atccagaccg accacactct   1800
cgcccgcgac tcccgcaccg cttgcgagtg gcagtcgttc gtcaacaacc agtccaagct   1860
cgtctccgac ttccagttca tcttccacgc cctcacccag ctcggccagg acccgaacgc   1920
gatgaccgac tgctcggatg tcatcccgat ctcgaagccc atccccggca accttccgtt   1980
ctcgttcttc ccccctggca agagcatgaa ggatgttgag caggctgtag tatccgattc   2040
agtccttgtc gcagagctta tgctgacggc ttctgcagtg cgccgagacc cccttcccca   2100
```

-continued

```
gcctcgtcac tctccccggc cccgcgacct ctgtcgctcg catgtgagta tctccgacgg   2160
tctatgaagc ccccagctga catattcctc ttccagcccc ccgccgccgg gtgcttaagt   2220
cattctatcg gtcatctttg gctgaaacgg agtatttgga atacggctca ctcgtaacgg   2280
taacttgcgc tcaagtgttt agaaatgtct cctttgtatc tacgcgattg gtccgctttt   2340
gacgatagat cgttactgtg ttcattgaaa ttctcgtccg cgcgccctgg agcgaaccgg   2400
ttagcattgc cacacgagag ctcttccgtt gctccaactc gagctgtaat ggtccaacgc   2460
tccacgctac atcaatttaa cctctcatgg gtacggtgta ttcggcaagt ttatctcaca   2520
taataagagg cacgctatca ttcgacgata caagaacatg agccttcgct tcgtttatga   2580
tattggttca ctgtcgagct aatttctgag ggttagcgct ctgacatgat cagctacagg   2640
aacggaggcc gtaccttgaa tgtgcccata aacccgctgt cttattcttc tcaaattgat   2700
tcttcatgtt tgaatcacgt ttgcaggtgc attcgtgtac ctgcggcgcg tacacgcggt   2760
atgtattggt cgcaaatcgc atcatggtga gatcttgctc ttcactcttg aagttgctac   2820
cgtataccac catgtgcagg aattctcgta catccctgtt tctcctcgaa tgtatgtgga   2880
gccagggaaa ccctaacccc ggattctgct gagatgcgtc gatgcacgca gccgtagcgg   2940
aggtccgtga ggtccgctcc ggccacgaag caggggccgt cctgaccggt cgaaggtcat   3000
gtcgtgcgac atagtcggct tccaggagga cgatatcgac caatacgtcg aaaggaggag   3060
actgcgggtc taggctggac gctgtttgcg agggcccggg ggagaacgag gccattggga   3120
gtcagcgaga ttattgaata gtcgaagggt attcattgag tcactaaggg aaacacttct   3180
gagccgctgg tagtacttgt gtatgcccgg gttctgcgcc tgataattag cctcgctcct   3240
ccgttgacgt tgggttttgg caataggaca tcaccacttt caccacgcgg acgcaatgcg   3300
aagggcacga gtggtatctc aatagctagt taccttccaa gaccctcaat catgatcgga   3360
agaagaggat gtgcaccgat atttcataag cccacggcag atatcgtaag agagtagacg   3420
aatgagattc gtagttaggt gcagagatac gatgaatgaa atctagtaaa gccgaagttc   3480
cgtcacgagt tagccggcca ccgttacagt cggtttgagg agtattctgt atggcatcat   3540
ttaagcaccc ggaggcggag ggctggagaa ggagcatgtc agcccagatt gcatttcctg   3600
aaagatctca tggattgtac tcacatgcgc tggacggacg tctcggggcc cgggagagtg   3660
gtgagagtcg ggaagggggt ctccgcacac tgtcatgcga tgttcagcag ccactctact   3720
gcatggtggg gtgaaatacg caccgcctgc tcaacgtcct tgatggtctt gccagcgggg   3780
aagaacgaga atgggaggtt gccagggatg ggcttggact gcgggataac atccgagcag   3840
tcggtcatcg cgttcgggtc ctggccgagc tgggtgaggg cgaggaagat gaactggaag   3900
tcatcgacga gcttggactg gttgttgacg aaggactgcc attcacacgc cgtgcgcgag   3960
tcgcgggcga tagtgtggtc ggactggatg cgaatttcgc cagggagcgg cgactcgacc   4020
tcgccttggt tgccaccaga gccggggaag gcggtaccac gaagctgagt ctcgacgaag   4080
aactgggagt cgaagattcc gggggtcgag tcaaagggca gaccctggac ggtcgggtcg   4140
acgtcgttca ccgctgcgac ggagtgcctg tcgaggtctc aggaagggag tgtcgaagtc   4200
aacagtgagt gacttacgcg gagagcatcc agacaagctc gagctcatcg aactcgcctg   4260
cgtcgttgac acggttgatg atttggtcga cagtgtctgc atgctagtca gtatagaccg   4320
cacctaactg cttggataag accacttacg gaagggctcg gggacaaggc catcaggagc   4380
gggctgggta gctaaagcag acagttagtt cgtaccatcc gcaaagcgag ttttgcaggt   4440
ataccaggtg cacgaccagt gaagaagttc atctgcgggg caccagggca gttgctgagc   4500
```

-continued gcgacacgac cagcgaaggc gatgaagtca ccaggggtga caccgtgctt ctgaacgaat 4560
ggcttctgga gcttgacgat ctcgtcgaga ccgatgttag ggtggaacgc agtctcgata 4620
tcgtcgaaga tcatgatgga gccgtcagca ccaccgccgc tgcaaggagg gatcagcaaa 4680
cgactaggtg gcgcaacgcg ggtggcaact tacccgaact tgccctgtgc ctccatggcg 4740
ggcgaaattg cgatggagtc gtggaagacg ctgggcgggg tgttcaaaca tgcatagcag 4800
gagatcgcga cgggatcact cacagacgaa tcgactcgtg cgcctcagcg ccgcactggc 4860
cgccgtggaa caggttctgc tggatatcat ccaggacgtc gaaccaagcg cagcacgacg 4920
catcgccgac ggtcttgccg ttggaacagg tggcgcgctt ctcgatcacc gcagccgctg 4980
cacaagacga cgttcagcat gcagtccact ggtcaacgct aactgcgatg ggcataccgt 5040
tcgcagccga gagcaagaga gcgagagaga tagctgcgaa gagctgcttg aaggccatgt 5100
ccgctgtgtt gctggtgctg agtgggactg aagagactgg atgtctgagg gactgcggtg 5160
gtcctgtcgc ccttttatac cctaggcgtg gtcgacgtcc tggtattgtt cgccgtagaa 5220
cagtgtcgaa tcgacgtgac gcggtgcgcg gacatgcacg acactgcgcc agccaatgag 5280
gacgctgcca aaacgcagcc tgtgagcgag ttggtgcggt gccggcaacc atcaccgact 5340
cgtctcacat ttgggccact gcgtcgagcg cagttcgcgc cggcaccgct gttgaatagc 5400
acgcgagctc tgcaagaaag aatagggcgg cccatgagaa cagaaatccg agtcagagga 5460
attaactgcg cgtgccgatg agtcttgaca tgaggatgat ctaacgaaga gaccttgcat 5520
tgagccgttt ccagtgctgc caggggtaat cagtcggcat tactgccaag tccggggatg 5580
tactgctagc tcactcccat cgcaatatgt caccgagtat tgcctttgtg aacataccat 5640
tgattcggtc ccgatcatgc acgaacgact cccgcaaagt ggggccagtg actatcacgt 5700
ccgtgctcag 5710

<210> SEQ ID NO 26
<211> LENGTH: 4707
<212> TYPE: DNA
<213> ORGANISM: Pyrococcus sp.

<400> SEQUENCE: 26
ggatccctct ctttttggta accccatacg tcattccctc aaccaaaact tcagcatcgt 60
tgcagtggtc agtgtgtctg tgggagatga agaggacgtc gatttttctg ggtctatct 120 tgtatctcca cattctaact aacgctccag gcccaggatc aacgtagatg tttttgctcg 180
ccttaatgaa gaagccacca gtggctcttg cctgcgttat cgtgacgaac cttccaccac 240
cgccaccgag aaaagttatc tctatcatct cacacctccc ccataacatc acctgctcaa 300
tttttaagcg ttcttaaagg cttaaatacg tgaatttagc gtaaattatt gagggattaa 360
gtatgatact tgacgctgac tacatcaccg aggatgggaa gccgattata aggattttca 420
agaaagaaaa cggcgagttt aaggttgagt acgacagaaa ctttagacct tacatttacg 480
ctctcctcaa agatgactcg cagattgatg aggttaggaa gataaccgcc gagaggcatg 540
ggaagatagt gagaattata gatgccgaaa aggtaaggaa gaagttcctg ggaggccga 600 ttgaggtatg gaggctgtac tttgaacacc ctcaggacgt tcccgcaata agggataaga 660
taagagagca ttccgcagtt attgacatct ttgagtacga cattccgttc gcgaagaggt 720
acctaataga caaaggccta attccaatgg aaggcgatga agagctcaag ttgctcgcat 780
ttgacataga aaccctctat cacgaagggg aggagttcgc gaaggggccc attataatga 840

-continued

```
taagctatgc tgatgaggaa gaagccaaag tcataacgtg gaaaaagatc gatctcccgt    900
acgtcgaggt agtttccagc gagagggaga tgataaagcg gttcctcaag gtgataaggg    960
agaaagatcc cgatgttata attacctaca acggcgattc tttcgacctt ccctatctag   1020
ttaagagggc cgaaaagctc gggataaagc taccccctggg aagggacggt agtgagccaa   1080
agatgcagag gcttggggat atgacagcgg tggagataaa gggaaggata cactttgacc   1140
tctaccacgt gattaggaga acgataaacc tcccaacata caccctcgag gcagtttatg   1200
aggcaatctt cggaaagcca aaggagaaag tttacgctca cgagatagct gaggcctggg   1260
agactggaaa gggactggag agagttgcaa agtattcaat ggaggatgca aaggtaacgt   1320
acgagctcgg tagggagttc ttcccaatgg aggcccagct ttcaaggtta gtcggccagc   1380
ccctgtggga tgtttctagg tcttcaactg gcaacttggt ggagtggtac ctcctcagga   1440
aggcctacga gaggaatgaa ttggctccaa acaagccgga tgagagggag tacgagagaa   1500
ggctaaggga gagctacgct gggggatacg ttaaggagcc ggagaaaggg ctctgggagg   1560
ggttagtttc cctagatttc aggagcctgt acccctcgat aataatcacc cataacgtct   1620
caccggatac gctgaacagg gaagggtgta gggaatacga tgtcgcccca gaggttgggc   1680
acaagttctg caaggacttc ccggggttta tccccagcct gctcaagagg ttattggatg   1740
aaaggcaaga aataaaaagg aagatgaaag cttctaaaga cccaatcgag aagaagatgc   1800
ttgattacag gcaacgggca atcaaaatcc tggcaaacag cattttaccg gaagaatggg   1860
ttccactaat taaaaacggt aaagttaaga tattccgcat tggggacttc gttgatggac   1920
ttatgaaggc gaaccaagga aaagtgaaga aaacggggga tacagaagtt ttagaagttg   1980
caggaattca tgcgttttcc tttgacagga agtccaagaa ggcccgtgta atggcagtga   2040
aagccgtgat aagacaccgt tattccggaa atgtttatag aatagtctta aactctggta   2100
gaaaaataac aataacagaa gggcatagcc tatttgtcta taggaacggg gatctcgttg   2160
aggcaactgg ggaggatgtc aaaattgggg atcttcttgc agttccaaga tcagtaaacc   2220
taccagagaa aagggaacgc ttgaatattg ttgaacttct tctgaatctc tcaccggaag   2280
agacagaaga tataatactt acgattccag ttaaaggcag aaagaacttc ttcaagggaa   2340
tgttgagaac attacgttgg atttttggtg aggaaaagag agtaaggaca gcgagccgct   2400
atctaagaca ccttgaaaat ctcggataca taaggttgag gaaaattgga tacgacatca   2460
ttgataagga ggggcttgag aaatatagaa cgttgtacga gaaacttgtt gatgttgtcc   2520
gctataatgg caacaagaga gagtatttag ttgaatttaa tgctgtccgg gacgttatct   2580
cactaatgcc agaggaagaa ctgaaggaat ggcgtattgg aactagaaat ggattcagaa   2640
tgggtacgtt cgtagatatt gatgaagatt ttgccaagct tcttggctac tatgtgagcg   2700
agggaagtgc gaggaagtgg aagaatcaaa ctggaggttg gagttacact gtgagattgt   2760
acaacgagaa cgatgaagtt cttgacgaca tggaacactt agccaagaag tttttttggga   2820
aagtcaaacg tggaaagaac tatgttgaga taccaaagaa aatggcttat atcatctttg   2880
agagcctttg tgggactttg gcagaaaaca aaagggttcc tgaggtaatc tttacctcat   2940
caaagggcgt tagatgggcc ttccttgagg gttatttcat cggcgatggc gatgttcacc   3000
caagcaagag ggttcgccta tcaacgaaga gcgagctttt agtaaatggc cttgttctcc   3060
tacttaactc ccttggagta tctgccatta agcttggata cgatagcgga gtctacaggg   3120
tttatgtaaa cgaggaactt aagtttacgg aatacagaaa gaaaaagaat gtatatcact   3180
ctcacattgt tccaaaggat attctcaaag aaacttttgg taaggtcttc cagaaaaata   3240
```

```
taagttacaa gaaatttaga gagcttgtag aaaatggaaa acttgacagg gagaaagcca   3300

aacgcattga gtggttactt aacggagata tagtcctaga tagagtcgta gagattaaga   3360

gagagtacta tgatggttac gtttacgatc taagtgtcga tgaagatgag aatttccttg   3420

ctggctttgg attcctctat gcacataata gctattatgg gtattatggg tacgcaaaag   3480

cccgttggta ctgtaaggag tgcgcagaga gcgttacggc ctgggggagg gaatatatag   3540

agttcgtaag gaaggaactg gaggaaaagt tcgggttcaa agtcttatac atagacacag   3600

atggactcta cgccacaatt cctggggcaa aacccgagga gataaagaag aaagccctag   3660

agttcgtaga ttatataaac gccaagctcc cagggctgtt ggagcttgag tacgagggct   3720

tctacgtgag agggttcttc gtgacgaaga agaagtatgc gttgatagat gaggaaggga   3780

agataatcac taggggggctt gaaatagtca ggagggactg gagcgaaata gccaaagaaa   3840

cccaagcaaa agtcctagag gctatcctaa agcatggcaa cgttgaggag gcagtaaaga   3900

tagttaagga ggtaactgaa aagctgagca agtacgaaat acctccagaa aagctagtta   3960

tttacgagca gatcacgagg ccccttcacg agtacaaggc tataggtccg cacgttgccg   4020

tggcaaaaag gttagccgct agaggagtaa aggtgaggcc tggcatggtg atagggtaca   4080

tagtgctgag gggagacggg ccaataagca agagggctat ccttgcagag gagttcgatc   4140

tcaggaagca taagtatgac gctgagtatt acatagaaaa tcaggtttta cctgccgttc   4200

ttagaatatt agaggccttt gggtacagga aagaagacct caggtggcag aagactaaac   4260

agacaggtct tacggcatgg cttaacatca agaagaagta atgtttatgt actcgtaatg   4320

cgagtattaa gtgggtgatg agatggcagt attgagcata aggattccgg atgatctaaa   4380

agagaagatg aaggagtttg acataaactg gagtgaggag atcaggaagt tcataaaaga   4440

gaggatagag tatgaggaaa ggaagagaac ccttgagaaa gctctagaac ttctaaagaa   4500

tactccagga tcagtcgaga gaggattttc agcaagggca gtgagggagg atcgtgatag   4560

tcattgatgc atcaatccta gctaaaataa ttctaaaaga agagggctgg gaacagataa   4620

ctcttacacc gagcacgata actttggact atgcttttgt tgaatgtaca aacgcaatat   4680

ggaaggctgt caggcggaac aggatcc                                        4707
```

```
<210> SEQ ID NO 27
<211> LENGTH: 3180
<212> TYPE: DNA
<213> ORGANISM: Bacillus sp. NBL420

<400> SEQUENCE: 27

gcatttcttt aagtagtacg tgtatatgtt gtgcatgccc cttcaggaag ggtatagtca     60

ttggtcactt ttctcagttc cttcaagatg ctgcctgcgg cttcatgctc ttgttcaagg    120

acgtcgatcg cctgaaccgc ttctgccagg ctgtccattg atcgcgtctc ttcataggtc    180

gtcactttcg ggaaaatgag ttcctcttcc tgaaagagat ggtgttccag ttcagttttc    240

agctgatgga acaattgatg gacctgggcg agttccggat gatggatgcc gtgaacccgg    300

tagacttttg tgacaaagcc tgatagttca ggaagcacct catacaggta agcatggtgc    360

gtatgaatca catggtcgat cagctgtgaa tacggggctt cactccagtt cgtctctttt    420

gcgttcaatg cctttgtctc ttgatataat gtattgattt ttgctaagat ctcttcttca    480

tttaaatcct gttcttttat cgcttcaccg atcgggcggt tgcccccgca gcaaaagtcg    540

atgcgatatt ctttcagcaa ccggctggct cttggaaaac gcgtaacaat atcacctgtt    600
```

-continued

```
tttgtgtttt gattgttttt gacaagatca cggagtttat ccggaaaccg ttcatgaaga    660
aaaagcagac ggttgatgaa caagggcatg tataaacgaa aaaagtgccg aaatcaaact    720
tcggctattt gctgaattgc tattggtgcg cagggatatg gtgcgctttg atcatcgctg    780
tcgggtatct gattgtccca aaaacgatat tcccgttaat tttaatttta tcggtcgcag    840
gtggacaggc gattcttgaa acgtttgtcg gtgtcgcaac aaaacttgtc agctttttct    900
ctgatttaaa gaaataaacc attccaagcg gatggtttta ttttttttgac aataaagtga    960
cacaaacagc agagagaaca tgtccgcttt gtgaactttt tacagcgatt ttttcccggt   1020
tgccgcattt taggcagagg gaagacatta ttttgaagaa gaatcaggtt ttaaaatttt   1080
gaattgagag aaaaaggaag cacaaagtcc ccggtcatac ttttttagct tttcatcatt   1140
agcattcaga cctcccattt catacgaaaa gaggaaatag atagattttc aaaacgaaaa   1200
aaacgtgaaa tatggttgat agacaatcaa tgaatagttt ttttacaatc agtaacgtgc   1260
tacaagccaa gaaaggggtg aaaatgtctg ccagaaagtg tttttggaaa ataacatcat   1320
tggaggaaaa agaatgtcat acatgaaacg ttccatttct gtcttcatcg cctgcttcat   1380
ggtagcagca ctcggcatca gcggtatcat cgcacctaaa gcgtctgccg cttctcaaac   1440
acccgttgct gtaaacggac agctcacctt gaaaggtacg cagctcgtca atcaaaaagg   1500
aaaagcggtt cagctgaaag gaatcagttc acacgggctg cagtggtatg gcgattatgt   1560
caacaaagac tcgttaaaat ggctgagaga cgactggggc atcaatgtct tccgcgcggc   1620
tatgtatacg ggtgaaggcg gctatattga caatccgtcg gttaaaaaca aagtgaagga   1680
agccgtcgaa gcggcaaaag aactcggaat ctatgtgatc atcgactggc acatactgag   1740
cgacggcaat ccaaaccaaa acaaagcgaa agcaaaagag tttttcaacg aaatgtcaag   1800
gctttacggc aagacgccaa acgtcatttt tgaaattgcc aacgagccga acggcgatgt   1860
caactggaac cgtgacatta acccttacgc tgaagacatt ttgtccgtga tccgcaaaaa   1920
ttctccgaaa aatattgtga tcgttgggac aggcacttgg agccaagatg tcaacgatgc   1980
ggcggacaat cagctgaaag acggcaatgt tatgtacgcg ctccattttt atgcgggtac   2040
gcacggtcag tctttgcggg ataaagcaga ctatgcactc agcaaaggag cgccgatttt   2100
cgtcacagaa tggggaacga gcgatgcttc cggaaacggc ggtgtctacc tcgaccaatc   2160
cagggagtgg ctgaaatatt tagacagcaa aaaaatcagc tgggtaaact ggagcttgtg   2220
cgacaaacaa gagtcgtcag ctgctttaaa ctccggcgcc tctaaaaagg gaggatggtc   2280
tcaatccgac ttatcctcat caggtaaatt cgtcagggaa aacatccgca gcggatcaaa   2340
cggttcgtca ggagactctg gatcggattc gaaagggtca gatcaaaaag accagaaaaa   2400
ggatcaggat aaaccaggtc aagacagcgg cgctgcagcc aacacgatag cagtacaata   2460
cagagcgggg gacaacaatg taaacggcaa ccaaatccgc cctcagctca acattaaaaa   2520
caacagcaaa aaaaccgtgt ctttaaatcg aatcactgtc cgctatggta taaaacgaat   2580
cacaaaggac aaaattttga ctgcgactat gcccaaatcg gctgcagcaa actcacgcac   2640
aaattcgtcc aattaaaaaa agcggtaaac ggagcagaca cgtatcttga agtaggattt   2700
aaaaacggta cattagcgcc gggtgcaagt acaggcgaaa tccagatccg tcttcacaat   2760
gacaactgga gcaattatgc ccaaatcggc gactattcat tttcttcagg ttcaaacaca   2820
tttaaaaata cgaaaaaaat cacgttgtat gagaatggaa aactgatttg gggcgctgaa   2880
cctaaataac ggcactttaa cggacaccga atttggtgtc cgttttcgta tatattataa   2940
tggaaggaat gaggaatatt tttgtaaaca tgaaaggaga tggatgtatg aatgaaacat   3000
```

tgcagcaata catgatgctt gtcaaggaaa actacgacac gatcaatgga cctgattacg 3060
caggcaaaga ggaagacatt gaaaagcgaa aaaaacaaat cgagctttac gccaaaacgc 3120
tccagcaagg tttttcaaca gatgacgact atgagaattc gtaatcaggt catagctgtt 3180

<210> SEQ ID NO 28
<211> LENGTH: 3153
<212> TYPE: DNA
<213> ORGANISM: Artificial Sequence
<220> FEATURE:
<223> OTHER INFORMATION: Intein Modified Cellulase

<400> SEQUENCE: 28
agcattcaga cctcccattt catacgaaaa gaggaaatag atagattttc aaaacgaaaa 60
aaacgtgaaa tatggttgat agacaatcaa tgaatagttt ttttacaatc agtaacgtgc 120
tacaagccaa gaaaggggtg aaaatgtctg ccagaaagtg tttttggaaa ataacatcat 180
tggaggaaaa agaatgtcat acatgaaacg ttccatttct gtcttcatcg cctgcttcat 240
ggtagcagca ctcggcatca gcggtatcat cgcacctaaa gcgtctgccg cttctcaaac 300
acccgttgct gtaaacggac agctcacctt gaaaggtacg cagctcgtca atcaaaaagg 360
aaaagcggtt cagctgaaag gaatcagttc acacgggctg cagtggtatg gcgattatgt 420
caacaaagac tcgttaaaat ggctgagaga cgactggggc atcaatgtct tccgcgcggc 480
tatgtatacg ggtgaaggcg gctatattga caatccgtcg gttaaaaaca aagtgaagga 540
agccgtcgaa gcggcaaaag aactcggaat ctatgtgatc atcgactggc acatactgag 600
cgacggcaat ccaaaccaaa acaaagcgaa agcaaaagag tttttcaacg aaatgtcaag 660
gctttacggc aagacgccaa acgtcatttt tgaaattgcc aacgagccga acggcgatgt 720
caactggaac cgtgacatta acccttacgc tgaagacatt ttgtccgtga tccgcaaaaa 780
ttctccgaaa aatattgtga tcgttgggac aggcacttgg agccaagatg tcaacgatgc 840
ggcggacaat cagctgaaag acggcaatgt tatgtacgcg ctccattttt atgcgggtac 900
gcacggtcag tctttgcggg ataaagcaga ctatgcactc agcaaaggag cgccgatttt 960
cgtcacagaa tggggaacga gcgatgctag cattttaccg gaagaatggg ttccactaat 1020
taaaaacggt aaagttaaga tattccgcat tggggacttc gttgatggac ttatgaaggc 1080
gaaccaagga aaagtgaaga aaacggggga tacagaagtt ttagaagttg caggaattca 1140
tgcgttttcc tttgacagga agtccaagaa ggcccgtgta atggcagtga aagccgtgat 1200
aagacaccgt tattccggaa atgtttatag aatagtctta aactctggta gaaaaataac 1260
aataacagaa gggcatagcc tatttgtcta taggaacggg gatctcgttg aggcaactgg 1320
ggaggatgtc aaaattgggg atcttcttgc agttccaaga tcagtaaacc taccagagaa 1380
aagggaacgc ttgaatattg ttgaacttct tctgaatctc tcaccggaag agacagaaga 1440
tataatactt acgattccag ttaaaggcag aaagaacttc ttcaagggaa tgttgagaac 1500
attacgttgg atttttggtg aggaaaagag agtaaggaca gcgagccgct atctaagaca 1560
ccttgaaaat ctcggataca taaggttgag gaaaattgga tacgacatca ttgataagga 1620
ggggcttgag aaatatagaa cgttgtacga gaaacttgtt gatgttgtcc gctataatgg 1680
caacaagaga gagtatttag ttgaatttaa tgctgtccgg gacgttatct cactaatgcc 1740
agaggaagaa ctgaaggaat ggcgtattgg aactagaaat ggattcagaa tgggtacgtt 1800
cgtagatatt gatgaagatt ttgccaagct tcttggctac tatgtgagcg agggaagtgc 1860

-continued

```
gaggaagtgg aagaatcaaa ctggaggttg gagttacact gtgagattgt acaacgagaa   1920

cgatgaagtt cttgacgaca tggaacactt agccaagaag ttttttggga aagtcaaacg   1980

tggaaagaac tatgttgaga taccaaagaa aatggcttat atcatctttg agagcctttg   2040

tgggactttg gcagaaaaca aaagggttcc tgaggtaatc tttacctcat caaagggcgt   2100

tagatgggcc ttccttgagg gttatttcat cggcgatggc gatgttcacc caagcaagag   2160

ggttcgccta tcaacgaaga gcgagctttt agtaaatggc cttgttctcc tacttaactc   2220

ccttggagta tctgccatta agcttggata cgatagcgga gtctacaggg tttatgtaaa   2280

cgaggaactt aagtttacgg aatacagaaa gaaaaagaat gtatatcact ctcacattgt   2340

tccaaaggat attctcaaag aaacttttgg taaggtcttc cagaaaaata taagttacaa   2400

gaaatttaga gagcttgtag aaaatggaaa acttgacagg gagaaagcca aacgcattga   2460

gtggttactt aacggagata tagtcctaga tagagtcgta gagattaaga gagagtacta   2520

tgatggttac gtttacgatc taagtgtcga tgaagatgag aatttccttg ctggctttgg   2580

attcctctat gcacataatt ccggaaacgg cggtgtctac ctcgaccaat ccagggagtg   2640

gctgaaatat ttagacagca aaaaaatcag ctgggtaaac tggagcttgt gcgacaaaca   2700

agagtcgtca gctgctttaa actccggcgc ctctaaaaag ggaggatggt ctcaatccga   2760

cttatcctca tcaggtaaat tcgtcaggga aaacatccgc agcggatcaa acggttcgtc   2820

aggagactct ggatcggatt cgaaagggtc agatcaaaaa gaccagaaaa aggatcagga   2880

taaaccaggt caagacagcg gcgctgcagc caacacgata gcagtacaat acagagcggg   2940

ggacaacaat gtaaacggca accaaatccg ccctcagctc aacattaaaa acaacagcaa   3000

aaaaaccgtg tctttaaatc gaatcactgt ccgctatggt ataaaacgaa tcacaaagga   3060

caaaattttg actgcgacta tgcccaaatc ggctgcagca aactcacgca caaattcgtc   3120

caattaaaaa aagcggtaaa cggagcagac acg                                3153
```